(12) United States Patent
Pleschka et al.

(10) Patent No.: US 9,566,281 B2
(45) Date of Patent: Feb. 14, 2017

(54) MEK INHIBITORS IN THE TREATMENT OF VIRUS DISEASES

(71) Applicants: Westfaelische Wilhelms-Universitaet, Muenster (DE); Stephan Pleschka, Giessen (DE); Oliver Planz, Rottenburg (DE)

(72) Inventors: Stephan Pleschka, Giessen (DE); Oliver Planz, Rottenburg (DE); Stephan Ludwig, Muenster (DE)

(73) Assignee: ATRIVA THERAPEUTICS GmbH, Tübingen (DE)

(*) Notice: Subject to any disclaimer, the term of this patent is extended or adjusted under 35 U.S.C. 154(b) by 0 days.

(21) Appl. No.: 14/434,328

(22) PCT Filed: Oct. 8, 2013

(86) PCT No.: PCT/EP2013/070917
§ 371 (c)(1),
(2) Date: Apr. 8, 2015

(87) PCT Pub. No.: WO2014/056894
PCT Pub. Date: Apr. 17, 2014

(65) Prior Publication Data
US 2015/0224103 A1    Aug. 13, 2015

Related U.S. Application Data

(60) Provisional application No. 61/711,136, filed on Oct. 8, 2012.

(51) Int. Cl.
*A61K 31/195* (2006.01)
*A61K 31/35* (2006.01)
(Continued)

(52) U.S. Cl.
CPC ............ *A61K 31/535* (2013.01); *A61K 31/18* (2013.01); *A61K 31/185* (2013.01);
(Continued)

(58) Field of Classification Search
CPC .. A61K 31/437; A61K 31/416; A61K 31/519; A61K 31/4439; A61K 31/351
(Continued)

(56) References Cited

U.S. PATENT DOCUMENTS

| 2010/0137431 A1 | 6/2010 | Ludwig et al. |
| 2010/0239563 A1 | 9/2010 | Ludwig et al. |
| 2010/0249118 A1* | 9/2010 | Ibrahim ................ C07C 37/62 514/228.2 |

FOREIGN PATENT DOCUMENTS

WO    WO 2009/140853    11/2009

OTHER PUBLICATIONS

Droebner, K., et al., (2011) *Antiviral activity of the MEK-inhibitor U0126 against pandemic H1N1v and highly pathogenic avian influenza virus in vitro and in vivo*, Antiviral Research 92: 195-203.
(Continued)

*Primary Examiner* — Shengjun Wang
(74) *Attorney, Agent, or Firm* — Kagan Binder, PLLC

(57) ABSTRACT

The present invention relates to MEK inhibitors that are capable of displaying one or more beneficial therapeutic effects. The MEK inhibitors can be used in the prevention and/or treatment of viral infection. MEK inhibitors in combination with neuraminidase inhibitor compounds are capable of displaying one or more beneficial therapeutic effects in the treatment of viral diseases.

5 Claims, 20 Drawing Sheets

(51) Int. Cl.
A61K 31/24 (2006.01)
A61K 31/519 (2006.01)
A61K 31/415 (2006.01)
A61K 31/215 (2006.01)
A61K 31/44 (2006.01)
A61K 31/425 (2006.01)
A61K 31/535 (2006.01)
A61K 45/06 (2006.01)
A61K 31/325 (2006.01)
A61K 31/437 (2006.01)
A61K 31/4458 (2006.01)
A61K 31/52 (2006.01)
A61K 31/18 (2006.01)
A61K 31/185 (2006.01)
A61K 31/245 (2006.01)
A61K 31/353 (2006.01)
A61K 31/4184 (2006.01)
A61K 31/4375 (2006.01)
A61K 31/4412 (2006.01)
A61K 31/506 (2006.01)

(52) U.S. Cl.
CPC .......... *A61K 31/215* (2013.01); *A61K 31/245* (2013.01); *A61K 31/325* (2013.01); *A61K 31/353* (2013.01); *A61K 31/4184* (2013.01); *A61K 31/437* (2013.01); *A61K 31/4375* (2013.01); *A61K 31/44* (2013.01); *A61K 31/4412* (2013.01); *A61K 31/4458* (2013.01); *A61K 31/506* (2013.01); *A61K 31/519* (2013.01); *A61K 31/52* (2013.01); *A61K 45/06* (2013.01)

(58) Field of Classification Search
USPC ............ 514/300, 373, 259.4, 321, 459, 538, 563,514/507, 394, 349, 264.1
See application file for complete search history.

(56) References Cited

OTHER PUBLICATIONS

Hsing-Pang, H. and Hsu, J.T.A., (2007) *Strategies of Development of Antiviral Agents Against Influenza Virus Replication*, Current Pharmaceutical Design 13: 3531-3542.
Ludwig, Stephan, (2009) *Targeting cell signalling pathways to fight the flu: towards a paradigm change in anti-influenza therapy*, Journal of Antimicrobial Chemotherapy 64: 1-4.
Puzanov, I., et al., (2011) *VEMURAFENIB*, Drugs of the Future 36: 191-199.

* cited by examiner

MEK inhibitors inhibit the proliferation of
Influenza A viruses

Fig. 1

Combination Oseltamivir and PLX-4032 (1:1)

| | CI values for Oseltamivir + PLX-4032 (1:1) |
|---|---|
| ED50 | 0,2783 |
| ED75 | 0,3472 |
| ED90 | 0,4332 |
| ED95 | 0,5036 |

| | IC$_{50}$ (ng/ml) |
|---|---|
| Oseltamivir | 1,12 |
| PLX-4032 | 202,10 |
| Oseltamivir + PLX-4032 (1:1) | 1,68 |

Combination Oseltamivir and PLX-4032 (1:10)

|  | CI values for Oseltamivir + PLX-4032 (1:10) |
|---|---|
| ED50 | 0,2247 |
| ED75 | 0,2305 |
| ED90 | 0,2367 |
| ED95 | 0,2413 |

|  | IC$_{50}$ (ng/ml) |
|---|---|
| Oseltamivir | 1,12 |
| PLX-4032 | 202,10 |
| Oseltamivir + PLX-4032 (1:10) | 11,25 |

Combination Oseltamivir and GSK-1120212

|  | IC$_{50}$ (ng/ml) |
|---|---|
| Oseltamivir | 0,081 |
| GSK-1120212 | 29,600 |
| Oseltamivir + GSK-1120212 (1:10) | 9,271 |

|  | CI values for Oseltamivir + GSK-1120212 (1:10) |
|---|---|
| ED50 | 0,4874 |
| ED75 | 0,4758 |
| ED90 | 0,4648 |
| ED95 | 0,4576 |

Combination Oseltamivir and AZD-6244 (1:10)

| | IC$_{50}$ (ng/ml) |
|---|---|
| Oseltamivir | 0,06 |
| AZD-6244 | 377,23 |
| Oseltamivir + AZD-6244 (1:10) | 1,64 |

| | CI values for Oseltamivir + AZD-6244 (1:10) |
|---|---|
| ED50 | 0,1472 |
| ED75 | 0,2086 |
| ED90 | 0,2962 |
| ED95 | 0,3760 |

Combination Oseltamivir and AZD-6244 (1:100)

| | CI values for Oseltamivir + AZD-6244 (1:100) |
|---|---|
| ED50 | 0,1140 |
| ED75 | 0,1616 |
| ED90 | 0,2330 |
| ED95 | 0,2993 |

| | $IC_{50}$ (ng/ml) |
|---|---|
| Oseltamivir | 0,06 |
| AZD-6244 | 377,23 |
| Oseltamivir + AZD-6244 (1:100) | 107,76 |

*In vitro* studies with the MEK-Inhibitor CI-1040 against H5N1 influenza virus

Fig. 6

*In vitro* studies with the MEK-Inhibitor PD-0325901 against H5N1 influenza virus

Fig. 7

Oral treatment of influenza virus infected mice with CI-1040 or PD-03250901

*In vitro* studies with the MEK- Inhibitor AZD-8330 against H1N1pdm09 influenza virus
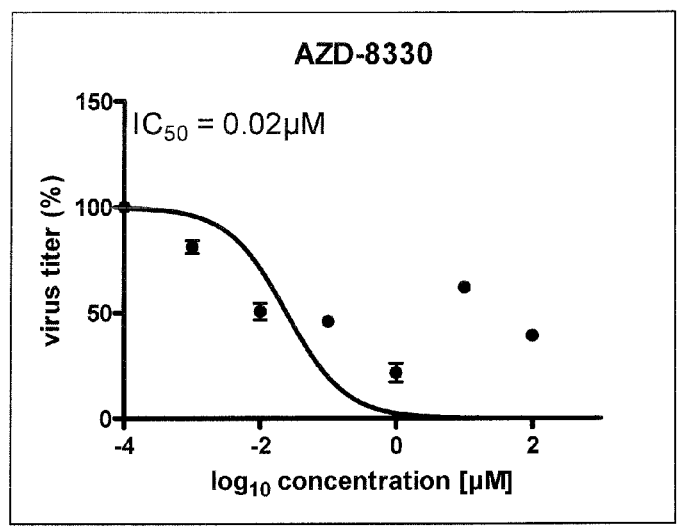
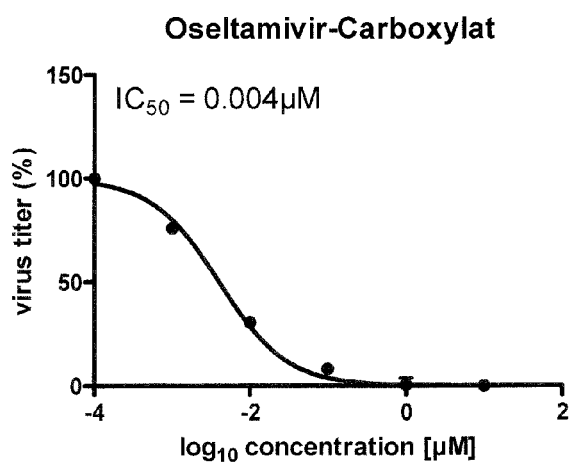
Fig.

Oral treatment of influenza virus infected mice with combination of PLX-4032 and Oseltamivir

*In vitro* studies with PLX-4032 (Vemurafenib)
against H7N9 influenza virus

Fig. 13

*In vitro* studies with PLX-4032 (Vemurafenib)
against H7N9 influenza virus

Syergistic Effect of simulatanious MEK- and Neuraminidase-
Inhibition against influenza B virus

Fig. 14

MEK INHIBITORS IN THE TREATMENT OF VIRUS DISEASES

This application claims benefit from International Application No. PCT/EP/2013/070917, which was filed on Oct. 8, 2013, which in turn claims priority to U.S. Provisional Patent Application Ser. No. 61/711,136, filed Oct. 8, 2012, the disclosures of which are incorporated herein by reference.

FIELD OF THE INVENTION

The present invention relates to MEK inhibitors that are capable of displaying one or more beneficial therapeutic effects. The MEK inhibitors can be used in the prevention and/or treatment of viral infection. MEK inhibitors in combination with neuraminidase inhibitor compounds are capable of displaying one or more beneficial therapeutic effects in the treatment of viral diseases.

BACKGROUND OF THE INVENTION

Infections with RNA or DNA viruses are a significant threat for the health of man and animal. For instance, infections with influenza viruses do still belong to the big epidemics of mankind and cause year for year a big number of casualties. In terms of the national economies, they are an immense cost factor, for instance due to unfitness for work. Infections with the Borna disease virus (BDV), which mainly affects horses and sheep, but which has also been isolated for humans and is connected to neurological diseases, equally have an enormous economic importance.

The problem of controlling in particular RNA viruses is the adaptability of the viruses caused by a high fault rate of the viral polymerases, which makes the production of suitable vaccines as well as the development of antiviral substances very difficult. Furthermore it has been found that the application of antiviral substances immediately directed against the functions of the virus, shows a good antiviral effect at the beginning of the treatment, but will quickly lead to the selection of resistant variants based on mutation. An example is the anti-influenza agent amantadine and its derivatives directed against a transmembrane protein of the virus. Within a short time after the application, resistant variants of the virus are generated. Other examples are the new therapeuticals for influenza infections inhibiting the influenza-viral surface protein neuraminidase. To these belongs for instance Relenza. In patients, Relenza-resistant variants have already been found (Gubareva et al., J Infect Dis 178, 1257-1262, 1998). Hopes placed in this therapeutical could therefore not be fulfilled.

Because of the very small genome and thus limited coding capacity for functions being necessary for the replication, all viruses are dependent to a high degree from functions of their host cells. By exertion of influence on such cellular functions being necessary for the viral replication, it is possible to negatively affect the virus replication in the infected cell. Herein, there is no possibility for the virus to replace the lacking cellular function by adaptation, in particular by mutations, in order to thus escape from the selection pressure. This could already be shown for the influenza A virus with relatively unspecific inhibitors against cellular kinases and methyl transferases (Scholtissek and Müller, Arch Virol 119, 111-118, 1991).

It is known in the art that cells have a multitude of signal transmission paths, by means of which signals acting on the cells are transmitted into the cell nucleus. Thereby the cell is capable to react to external stimuli and to react by cell proliferation, cell activation, differentiation, or controlled cell death. It is common to these signal transmission paths that they contain at least one kinase activating by phosphorylation at least one protein subsequently transmitting a signal. When observing the cellular processes induced after virus infections, it is found that a multitude of DNA and RNA viruses preferably activate in the infected host cell a defined signal transmission path, the so-called Raf/MEK/ERK kinase signal transmission path (Benn et al., J Virol 70, 4978-4985, 1996; Bruder and Kovesdi, J Virol 71, 398-404, 1997; Popik and Pitha, Virology 252, 210-217, 1998; Rodems and Spector, J Virol 72, 9173-9180, 1998). This signal transmission path is one of the most important signal transmission paths in a cell and plays a significant role in proliferation and differentiation processes. Growth factor-induced signals are transmitted by successive phosphorylation from the serine/threonine kinase Raf to the dual-specific kinase MEK (MAP kinase kinase/ERK kinase) and finally to the kinase ERK (extracellular signal regulated kinase). Whereas as a kinase substrate for Raf, only MEK is known, and the ERK isoforms were identified as the only substrates for MEK, ERK is able to phosphorylate a whole number of substrates. To these belong for instance transcription factors, whereby the cellular gene expression is directly influenced (Cohen, Trends in Cell Biol 7, 353-361, 1997; Robinson and Cobb, Curr. Opin. Cell Biol 9, 180-186, 1997; Treisman, Curr. Opin. Cell Biol 8, 205-215, 1996).

The drawback of prior art antiviral active substances is that they are either directed against a viral component and thus quickly lead to resistances (cf. amantadine), or act in a too broad and unspecific manner against cellular factors (for example methyl transferase inhibitors), and significant side effects are to be expected. Consequently, none of the substances being active against cellular factors is known to have been developed to a therapeutical for virus diseases. On the other hand, the inhibition of other kinases, for instance the inhibition of the kinase JNK of the MEKK/SEK/JNK signal transmission path, can increase the virus multiplication. Further it is known that the increased activation of again other kinases, for instance of the protein kinase C (PKC), inhibits the replication of viruses (Driedger and Quick, WO 92/02484).

With regard to the cellular processes induced after a virus infection, it is found that a multitude of DNA and RNA viruses activate, in the infected host cell, a defined signal transduction pathway, the so-called Raf/MEK/ERK kinase cascade.

This kinase cascade belongs to the most important signaling pathways in the cell and plays an essential role in proliferation and differentiation processes.

Growth-factor induced signals are transferred by successive phosphorylation from the serine/theorine kinase Raf to the dual specific kinase MEK (MAP kinase kinase/ERK kinase) and finally to the kinase ERK (extracellular signal regulated kinase). Whilst as a kinase substrate of Raf, only MEK is known, and the ERK isoforms have been identified for MEK as the only substrate, ERK can phosphorylate quite a number of substrates. Hereto belong for instance the phosphorylation of transcription factors, which leads to a direct modification of the cellular gene expression.

The investigation of this signaling pathway in cellular decision processes has led to the identification of several pharmalogical inhibitors, which inhibit the signaling pathway, among other positions, on the level of MEK, i.e. at the 'bottleneck' of the cascade.

The MEK inhibitor PD98059 inhibits the activation of MEK by the kinase Raf.

The MEK inhibitor PD184352 has been described (2-(2-chloro-4-iodo-phenylamino)-N-cyclopropylmethoxy-3,4-difluoro-benzamide), which with oral administration in the mouse model could efficiently inhibit the growth of colon carcinoma.

The MEK inhibitor AZD6244 (Selumetinib) is a drug being investigated for the treatment of various types of cancer, for example non-small cell lung cancer (NSCLC).

AZD8330 is an orally active, selective MEK inhibitor with an IC50 of 7 nM. AZD8330 has potential antineoplastic activity. AZD8330 specifically inhibits mitogen-activated protein kinase kinase 1 (MEK or MAP/ERK kinase1), resulting in inhibition of growth factor-mediated cell signaling and tumor cell proliferation.

The MEK inhibitor RDEA-119 (BAY-869766) has been shown to be a potent, selective, allosteric inhibitor of MEK1/2 for the treatment of cancer.

The MEK inhibitor GSK-1120212 (Trametinib) is a potent and selective allosteric inhibitor of the MEK1 and MEK2 (MEK1/2) enzymes with promising antitumor activity in a phase I clinical trial (ASCO 2010).

TAK-733 is a potent, selective, ATP-noncompetitive MEK allosteric site inhibitor with an 1050 of 3.2 nM.

The MEK inhibitor RO5126766 is a protein kinase inhibitor specific for the Raf and MEK mitogen-activated protein kinases (MAPKs) with potential anti-neoplastic activity. Raf/MEK dual kinase inhibitor RO5126766 specifically inhibits the kinase activities of Raf and MEK, resulting in the inhibition of target gene transcription that promotes malignant transformation of cells.

The MEK inhibitor AS703026 is a novel, highly selective and potent allosteric inhibitor of MEK1/2 which is currently under Phase II clinical trial for acute myeloid leukemia.

The MEK inhibitor PLX-4032 (Zelboraf® (Vemurafenib)) is market for the treatment of late-stage melanoma.

The MEK inhibitors CI-1040, PD0325901, AZD6244, GDC-0973, RDEA119, GSK1120212, AZD8330, RO5126766, RO4987655, TAK-733 and AS703026 are known in the art and, for example, described in Table 1 and shown in FIG. 4 of Fremin and Meloche (2010), J. Hematol. Oncol. 11; 3:8.

Neuraminidase (also known as sialidase, acylneuraminyl hydrolase, and EC 3.2.1.18) is an enzyme common among animals and a number of microorganisms. It is a glycohydrolase that cleaves terminal alpha-ketosidically linked sialic acids from glycoproteins, glycolipids and oligosaccharides. Many of the microorganisms containing neuraminidase are pathogenic to man and other animals including fowl, horses, swine and seals. These pathogenic organisms include influenza virus.

Neuraminidase has been implicated in the pathogenicity of influenza virus. It is thought to help the elution of newly synthesized virons from infected cells and assist in the movement of the virus (through its hydrolase activity) through the mucus of the respiratory tract.

A class of specific anti-influenza agents, the neuraminidase inhibitors, has demonstrated inhibition of both influenza A and B viruses. Oseltamivir is used for the treatment of viral infections; however, it does not treat nasal congestion. Oseltamivir is the ethyl ester prodrug of the carbocyclic transition state sialic acid analog RO 64-0802 (GS4071), a potent and selective inhibitor of influenza A and B virus neuraminidases. Oral oseltamivir has been approved for treatment of acute influenza in the United States in 1999. It has demonstrated efficacy both in treating and preventing influenza illness.

Oseltamivir phosphate is a prodrug of oseltamivir carboxylate (oseltamivir), an inhibitor of the neuraminidase glycoprotein essential for replication of influenza A and B viruses. Oseltamivir is available from Roche Pharma™ AG (Switzerland). Alternatively, oseltamivir can be prepared according to the methods described in U.S. Pat. No. 5,763,483 to Bischofberger et al and U.S. Pat. No. 5,866,601 to Lew et al. About 10-15% of patients taking oseltamivir experience nausea and vomiting. Patients with kidney dysfunction should take lower doses.

Zanamivir (Relenza) is an orally inhaled powder currently approved in 19 countries for the treatment of, and in two for the prophylaxis of influenza A and B. Zanamivir is a competitive inhibitor of the neuraminidase glycoprotein, which is essential in the infective cycle of influenza viruses. It closely mimics sialic acid, the natural substrate of the neuraminidase. Over the last few years, a number of events have resulted in changes to the zanamivir prescribing information which now contains warnings of bronchospasm, dyspnea, rash, urticaria and allergic type reactions, including facial and oropharyngeal oedema.

Peramivir is a neuraminidase inhibitor, acting as a transition-state analogue inhibitor of influenza neuraminidase and thereby preventing new viruses from emerging from infected cells.

It is known that neuraminidase inhibitors are not effective for all influenza viruses and a resistance can be developed by new generation of influenza virus strain.

In view of the prior art, it is clear that there is the need of compounds and compositions effective in the treatment of virus diseases in particular in diseases caused by influenza virus.

DESCRIPTION OF THE INVENTION

This need is obviated by using the MEK inhibitor compounds of the invention or their combination with one or more such as one, two, three, etc. neuraminidase inhibitors.

When used herein, a "MEK inhibitor" may also be designated as a Mitogen Activated Proteinkinase (MAPK) kinase inhibitor. It is known that in a MAPK pathway, a MAPK kinase kinase (MAPKKK) activates a MAPK kinase (MAPKK) which in turn activates a MAPK which transduces a signal to, for example, a transcription factor or other kinases or effector/signal transducing protein; see, for example, FIG. 1 of Fremin and Meloche, cited herein above. MEK inhibitors of the invention preferably inhibit MEK1/2 of a subject, such as a mammal or bird as described herein. However, it may be that a MEK inhibitor of the invention does not only inhibit a MEK, preferably MEK1/2, but also its upstream kinase (i.e. MAPKKK), thereby exerting a dual inhibition. Without being bound by theory, PLX-4032 may be such a dual inhibitor. Hence, a MEK inhibitor of the invention may in a preferred aspect by a dual inhibitor, thereby inhibiting a MEK, preferably MEK1/2 and the corresponding upstream MAPKKK. MEK1/2 is the MAPKK in the Ras/Raf pathway, whereby Ras/Raf acts as MAPKKK and ERK1/2 acts as MAPK.

When used herein, the term "MEK inhibitor" includes one MEK inhibitor, such as one of the MEK inhibitors as disclosed herein, but one or more MEK inhibitors, such as two, three, four, five, or more MEK inhibitors, for example, selected from the MEK inhibitors disclosed herein.

A neuraminidase inhibitor is an antiviral drug targeted at influenza virus, which works by blocking the function of the viral neuraminidase protein, thus preventing the virus from binding to a cell it aims to infect and/or preventing the virus from reproducing by budding from the host cell, since the newly produced viruses cannot bud off from the cell in which they have replicated. Preferred neuraminidase inhibitors are oseltamivir, zanamivir, peramivir, or a pharmaceutically acceptable salt of any of these substances, such as oseltamivir phosphate, oseltamivir carboxylate, etc.

SUMMARY OF THE INVENTION

The present invention can be summarized by the following items:
1. A method for the prophylaxis and/or treatment of a viral disease, comprising administering a MEK inhibitor or a pharmaceutically acceptable salt thereof to a patient in need thereof.
2. The method according to item 1 wherein the viral disease is an infection caused by a negative RNA strand virus.
3. The method according to item 2, wherein the virus is influenza virus.
4. The method according to item 1 or 2 or 3, wherein the MEK inhibitor is selected from the group: PLX-4032, AZD6244, AZD8330, AS-703026, GSK-1120212, RDEA-119, RO-5126766, RO-4987655, CI-1040, PD-0325901, GDC-0973, TAK-733, PD98059 and PD184352 or a pharmaceutically acceptable salt thereof.
5. The method according to any one of the preceding items wherein the MEK inhibitor a pharmaceutically acceptable salt thereof is administered in combination with a neuraminididase inhibitor or a pharmaceutically acceptable salt thereof.
6. The method according to item 5 wherein the MEK inhibitor or a pharmaceutically acceptable salt thereof is administered contemporaneously, previously or subsequently to the neuraminididase inhibitor a pharmaceutically acceptable salt thereof.
7. The method according to item 5 or 6 wherein the neuraminidase inhibitor is selected from oseltamivir, oseltamivir phosphate, zanamivir or peramivir a pharmaceutically acceptable salt thereof.
8. A pharmaceutical composition comprising a MEK inhibitor or a pharmaceutically acceptable salt thereof and a neuraminidase inhibitor or a pharmaceutically acceptable salt thereof.
9. A pharmaceutical composition comprising a MEK inhibitor and a neuraminidase inhibitor or a pharmaceutically acceptable salt thereof for use as a medicament.
10. The pharmaceutical composition of item 8 or 9 wherein the MEK inhibitor is selected from PLX-4032, AZD6244, AZD8330, AS-703026, GSK-1120212, RDEA-119, RO-5126766, RO-4987655, CI-1040, PD-0325901, GDC-0973, TAK-733, PD98059 and PD184352, or a pharmaceutically acceptable salt thereof.
11. The pharmaceutical composition of item 8 or 9 or 10 wherein the neuraminidase inhibitor is selected from oseltamivir, oseltamivir phosphate, zanamivir or peramivir.
12. The pharmaceutical composition as defined in item 8 or 10 or 11 for use in the prophylaxis and/or treatment of a viral disease.
13. A MEK inhibitor compound for use in the prophylaxis and/or treatment of a viral disease.
14. A compound selected from PLX-4032, AZD6244, AZD8330, AS-703026, GSK-1120212, RDEA-119, RO-5126766, RO-4987655, CI-1040, PD-0325901, GDC-0973, TAK-733, PD98059 and PD184352, or a pharmaceutically acceptable salt thereof for use in the prophylaxis and/or treatment of a viral disease.
15. The compound for use according to item 14 selected from PLX-4032, AZD6244, AZD8330, GDC-0973, RDEA119, GSK1120212, RO51267766, RO4987655, TAK-733, and AS703026 a pharmaceutically acceptable salt thereof.
16. The compound for use according to item 14 or 15 wherein the viral diseases is an infection caused by negative RNA strand virus.
17. The compound for use according to item 16 wherein the virus is an influenza virus.
18. The compound for use according to item 13 or 14 or 15 or 16 or 17 wherein the compound is administered in combination with a neuraminidase inhibitor a pharmaceutically acceptable salt thereof.
19. The compound for use according to item 18 wherein the neuraminidase inhibitor is selected from oseltamivir, oseltamivir phosphate, zanamivir or peramivir.
20. A MEK inhibitor or a pharmaceutically acceptable salt thereof for use in a method for the prophylaxis and/or treatment of a viral disease, wherein said MEK inhibitor is selected from the group consisting of PLX-4032, AZD6244, AZD8330, AS-703026, GSK-1120212, RDEA-119, RO-5126766, RO-4987655, CI-1040, PD-0325901, GDC-0973, TAK-733, PD98059 and PD184352, or a pharmaceutically acceptable salt thereof.
21. The MEK inhibitor or a pharmaceutically acceptable salt thereof for the use according to item 20 wherein the viral disease is an infection caused by a negative RNA strand virus.
22. The MEK inhibitor or a pharmaceutically acceptable salt thereof for the use according to item 21, wherein the virus is influenza virus.
23. The MEK inhibitor or a pharmaceutically acceptable salt thereof for the use according to item 22, wherein the influenza virus is influenza A virus or influenza B virus.
24. The MEK inhibitor or a pharmaceutically acceptable salt thereof for the use according to any one of the preceding items, wherein the MEK inhibitor a pharmaceutically acceptable salt thereof is administered in combination with a neuraminididase inhibitor or a pharmaceutically acceptable salt thereof.
25. The MEK inhibitor or a pharmaceutically acceptable salt thereof for the use according to item 24 wherein the MEK inhibitor or a pharmaceutically acceptable salt thereof is administered contemporaneously, previously or subsequently to the neuraminididase inhibitor a pharmaceutically acceptable salt thereof.
26. The MEK inhibitor or a pharmaceutically acceptable salt thereof for the use according to item 24 or 25 wherein the neuraminidase inhibitor is selected from oseltamivir, oseltamivir phosphate, zanamivir or peramivir a pharmaceutically acceptable salt thereof.
27. A pharmaceutical composition comprising a MEK inhibitor or a pharmaceutically acceptable salt thereof and a neuraminidase inhibitor or a pharmaceutically acceptable salt thereof.

28. A pharmaceutical composition comprising a MEK inhibitor and a neuraminidase inhibitor or a pharmaceutically acceptable salt thereof for use as a medicament.

29. The pharmaceutical composition of item 27 or 28 wherein the MEK inhibitor is selected from PLX-4032, AZD6244, AZD8330, AS-703026, GSK-1120212, RDEA-119, RO-5126766, RO-4987655, CI-1040, PD-0325901, GDC-0973, TAK-733, PD98059 and PD184352, or a pharmaceutically acceptable salt thereof.

30. The pharmaceutical composition of item 27, 28 or 29 wherein the neuraminidase inhibitor is selected from oseltamivir, oseltamivir phosphate, zanamivir or peramivir.

31. The pharmaceutical composition as defined in any one of items 27 to 30 for use in the prophylaxis and/or treatment of a viral disease.

Method of Treatment

The invention is based on the object to provide substances for application in the prevention or therapy of viral diseases, in particular prevention and/or therapy against intracellular and/or intranuclear-replicating negative strand RNA viruses, such substances not being immediately directed against functions of the virus, but selectively inhibiting a cellular enzyme, and inhibiting via this selective effect the viral replication of viruses.

Surprisingly, it has been found that this object can be achieved by a kinase cascade inhibitor according to the invention or in particular by drugs containing a MEK inhibitor compound.

Hence, in an aspect, the present invention provides a method for the prophylaxis and/or treatment of a viral disease comprising administering a MEK inhibitor to a patient in need thereof.

In an aspect, the method of the invention is for the prophylaxis and/or treatment of a viral disease which is an infection caused by negative RNA strand virus. More preferably, the viral disease is caused by an influenza virus, even more preferably is caused by influenza A or B viruses. Influenza viruses are for example H1N1, H5N1, H7N7, H7N9.

The MEK inhibitors of the invention are selected preferably from PLX-4032, AZD6244, AZD8330, AS-703026, GSK-1120212, RDEA-119, RO-5126766, RO-4987655, CI-1040, PD-0325901, GDC-0973, TAK-733, PD98059 and PD184352.

Structural formula I

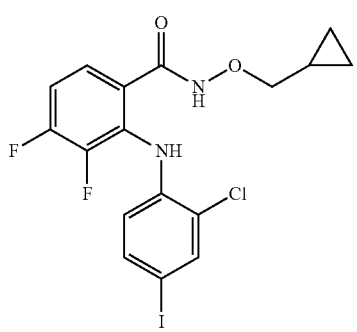

CI-1040
2-(2-chloro-4-iodophenylamino)-
N-(cyclopropylmethoxy)-
3,4-difluorobenzamide Structural formula II

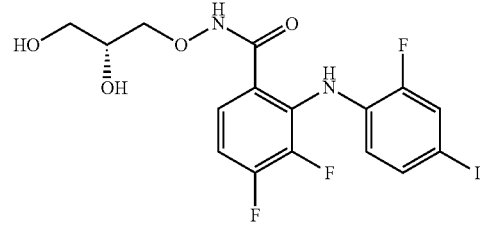

PD0325901
(R)-N-(2,3-dihydroxypropoxy)-
3,4-difluoro-2-(2-fluoro-4-iodo-
phenylamino)benzamide Structural formula III

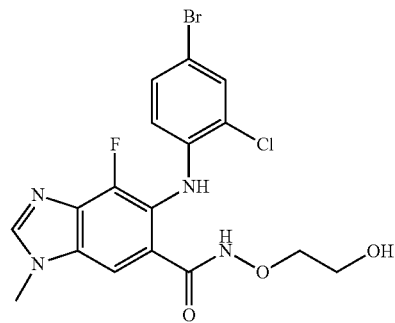

AZD6244
6-(4-bromo-2-chlorophenylamino)-
7-fluoro-N-(2-hydroxyethoxy)-3-methyl-
3H-benzo[d]imidazole-5-carboxamide Structural formula IV

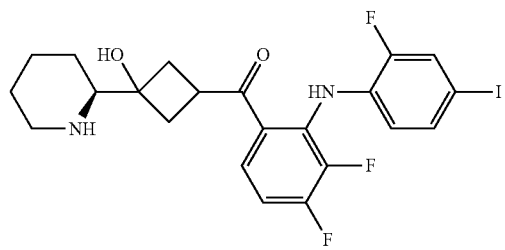

GDC-0973
[3,4-difluoro-2-[(2-fluoro-4-iodophenyl)amino]phenyl]
[3-hydroxy-3-[(2S)-2-piperidinyl]-1-azetidinyl]methanone Structural formula V

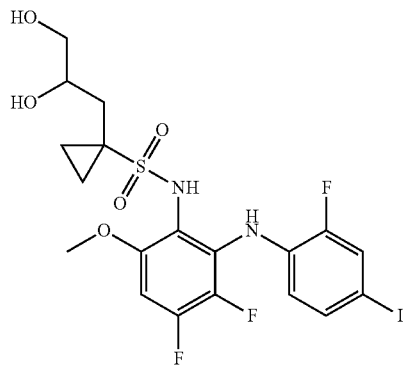

RDEA-119
(S)-N-(3,4-difluoro-2-(2-fluoro-4-iodophenyl-
amino)-6-methoxyphenyl)-1-(2,3-dihydroxypropyl)
cyclopropane-1-sulfonamide Structural formula VI GSK-1120212
N-(3-(3-cyclopropyl-5-(2-fluoro-4-iodophenylamino)-
6,8-dimethyl-2,4,7-trioxo-3,4,6,7-tetrahydropyrido
[4,3-d]pyrimidin-1(2H)-yl)phenyl)acetamide Structural formula VII AZD8330
2-(2-fluoro-4-iodophenylamino)-N-
(2-hydroxyethoxy)-1,5-dimethyl-6-oxo-
1,6-dihydropyrine-3-carboxamide Structural formula VIII

RO5126766
C20H16FN5O5S

Structurual formula IX

RO4987655
C20H19F3IN3O5

Structural formula X

TAK-733
(R)-3-(2,3-dihydroxypropyl)-6-fluoro-5-
(2-fluoro-4-iodophenylamino)-8-methylpyrido
[2,3-d]pyrimidine-4,7(3H,8H)-dione Structural formula XI Zelboraf (vemurafenib)
PLX-4032
N-[3-[[5-(4-Chlorophenyl)-1H-pyrrolo
[2,3-b]pyridin-3-yl]carbonyl]-2,4-difluorophenyl]-
1-propanesulfonamide Structural formula XII AS703026
(S)-N-(2,3-dihydroxypropyl)-3-
(2-fluoro-4-iodophenylamino)
isonicotinamide Structural formula XIII PD98059
2-(2-amino-3-methoxyphenyl)-4H-chromen-4-one Structural formula XIV

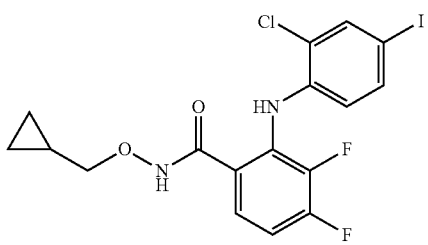

PD184351
2-(2-chloro-4-iodophenylamino)-
N-(cyclopropylmethoxy)-
3,4-difluorobenazmide More preferably, they are selected from PLX-4032, AZD6244, AZD8330, GDC-0973, RDEA119, GSK1120212, RO51267766, RO4987655, TAK-733, and AS703026. Even more preferably, they are selected from AZD6244, AZD8330, GSK1120212 and PLX-4032 or from PD-0325901, AZD-6244, AZD-8330 and RDEA-119. These MEK inhibitors are known in the art and, for example, described in Table 1 of Fremin and Meloche (2010), J. Hematol. Oncol. 11; 3:8.

Indeed, as demonstrated in the appended Examples, the MEK. Inhibitors AS-703026, AZD-6244, AZD-8033, PLX-4032, GSK-1120212, RDEA-119, RO-5126766, CI-1040, PD-0325901 are highly active against influenza A or B virus as single agent. Also, as demonstrated in the appended Examples, the MEK inhibitors disclosed herein show a synergistic effect in combination with a neuraminidase inhibitor, such as oseltamivir, both against influenza A virus and/or influenza B virus.

The subject or patient of the invention is a mammal or a bird. Examples of suitable mammals include, but are not limited to, a mouse, a rat, a cow, a goat, a sheep, a pig, a dog, a cat, a horse, a guinea pig, a canine, a hamster, a mink, a seal, a whale, a camel, a chimpanzee, a rhesus monkey and a human. Examples of suitable birds include, but are not limited to, a turkey, a chicken, a goose, a duck, a teal, a mallard, a starling, a Northern pintail, a gull, a swan, a Guinea fowl or water fowl, to name a few. Human patients are a particular embodiment of the present invention.

In the method of the invention, the MEK inhibitor may be administered orally, intravenously, intrapleurally, intramuscularly, topically or via inhalation. Preferably, the MEK inhibitor is administered via nasal inhalation or orally.

The pharmaceutical composition comprising the MEK inhibitor may be in the form of orally administrable suspensions or tablets; nasal sprays, sterile injectable preparations (intravenously, intrapleurally, intramuscularly), for example, as sterile injectable aqueous or oleaginous suspensions or suppositories. When administered orally as a suspension, these compositions are prepared according to techniques available in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art. The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

In the method of the invention, the MEK inhibitor is administered in a therapeutically effective amount.

MEK Inhibitor Compounds for Use

In an aspect, the present invention provides a MEK inhibitor for use in (a method for) the prophylaxis and/or treatment of a viral disease.

In an aspect, the present invention provides a MEK inhibitor for use in (a method for) the prophylaxis and/or treatment of a viral disease comprising administering a MEK inhibitor to a subject or a patient in need thereof.

The viral disease is preferably an infection caused by negative RNA strand virus. More preferably, the viral disease is caused by an influenza virus, even more preferably the viral disease is caused by influenza A or B virus. Influenza viruses are for example: H1N1, H5N1, H7N7, H7N9.

The MEK inhibitors of the invention are selected preferably from PLX-4032, AZD6244, AZD8330, AS-703026, GSK-1120212, RDEA-119, RO-5126766, RO-4987655, CI-1040, PD-0325901, GDC-0973, TAK-733, PD98059 and PD184352. More preferably are selected from AZD6244, GDC-0973, RDEA119, GSK1120212, AZD8330, RO51267766, RO4987655, TAK-733, PLX-4032 and AS703026. Even more preferably they are selected from GSK1120212, AZD6244, PLX-4032 or from PD-0325901, AZD-6244, AZD-8330 and RDEA-119.

The MEK inhibitor for use in the present invention may be administered orally, intravenously, intrapleurally, intramuscularly, topically or via inhalation. Preferably, the MEK inhibitor is administered via nasal inhalation or orally.

The MEK inhibitor for use is administered in a therapeutically effective amount.

The pharmaceutical composition comprising the MEK inhibitor for use may be in the form of orally administrable suspensions or tablets; nasal sprays, sterile injectable preparations (intravenously, intrapleurally, intramuscularly), for example, as sterile injectable aqueous or oleaginous suspensions or suppositories. When administered orally as a suspension, these compositions are prepared according to techniques available in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, di-calcium phosphate, starch, magnesium stearate and lactose and/or other excipients, binders, extenders, disintegrants, diluents, and lubricants known in the art. The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

Pharmaceutical Composition for Use

In an aspect, the present invention provides a pharmaceutical composition comprising a MEK inhibitor for use in the prophylaxis and/or treatment of a viral disease.

In an aspect, the present invention provides a pharmaceutical composition comprising a MEK inhibitor for use in the prophylaxis and/or treatment of a viral disease comprising administering a MEK inhibitor to a patient in need thereof.

The viral disease is preferably an infection caused by negative RNA strand virus. More preferably, the viral disease is caused by an influenza virus, even more preferably the viral disease is caused by influenza A or B virus. Influenza viruses are for example: H1N1, H5N1, H7N7, H7N9.

The MEK inhibitors of the pharmaceutical composition for the use of the invention are selected preferably from PLX-4032, AZD6244, AZD8330, AS-703026, GSK-1120212, RDEA-119, RO-5126766, RO-4987655, CI-1040, PD-0325901, GDC-0973, TAK-733, PD98059 and PD184352. More preferably are selected from AZD6244, GDC-0973, RDEA119, GSK1120212, AZD8330, RO51267766, RO4987655, TAK-733, PLX-4032 and AS703026. Even more preferably they are selected from GSK1120212, AZD6244, PLX-4032 or from PD-0325901, AZD-6244, AZD-8330 and RDEA-119.

The pharmaceutical composition for the use of the invention and comprising a MEK inhibitor is administered to a patient which is a mammal or a bird. Examples of suitable mammals include, but are not limited to, a mouse, a rat, a cow, a goat, a sheep, a pig, a dog, a cat, a horse, a guinea pig, a canine, a hamster, a mink, a seal, a whale, a camel, a chimpanzee, a rhesus monkey and a human, with human being preferred. Examples of suitable birds include, but are not limited to, a turkey, a chicken, a goose, a duck, a teal, a mallard, a starling, a Northern pintail, a gull, a swan, a Guinea fowl or water fowl to name a few. Human patients are a particular embodiment of the present invention.

The pharmaceutical composition may be in the form of orally administrable suspensions or tablets; nasal sprays, sterile injectable preparations (intravenously, intrapleurally, intramuscularly), for example, as sterile injectable aqueous or oleaginous suspensions or suppositories. When administered orally as a suspension, these compositions are prepared according to techniques available in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, di-calcium phosphate, starch, magnesium stearate and lactose and/or other excipients, binders, extenders, disintegrants, diluents, and lubricants known in the art. The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. Preferably, the MEK inhibitors are administered orally or via nasal spray.

Combination Therapy

Surprisingly, the inventors have further found that the combined administration of a MEK inhibitor and a neuraminidase inhibitor creates unexpected synergies in preventing and/or treating viral diseases, in particular the combination of a MEK inhibitor and a neuraminidase inhibitor led to a synergistic affect in inhibiting influenza A virus and/or B virus. Indeed, as shown herein, the MEK inhibitors, CI-1040, GSK-1120212, PD-0325901, AZD-6244, AZD-8330, RDEA-119, PLX-4032 that are orally available and at least in a phase I clinical trial, some of them are even in a phase II clinical trial or even admitted for marketing, such as PLX-4032, against cancer demonstrate antiviral activity, both against influenza A virus and/or influenza B virus, in combination with a neuraminidase inhibitor, such as oseltamivir. Combination treatment increased the antiviral activity of oseltamivir significantly and resulted in a synergistic antiviral effect as determined by the Chou-Talalay method described herein. Taken together, the results demonstrate increased antiviral activity of oseltamivir after combination with MEK inhibitors. These data are promising for further preclinical in vitro and in vivo investigations on the way to developing new antiviral regimens against influenza Hence, the present invention provides a method for the prophylaxis and/or treatment of a viral disease comprising administering a MEK inhibitor in combination with a neuraminidase inhibitor to a patient in need thereof.

In the method of the invention, a MEK inhibitor and a neuraminidase inhibitor are administered contemporaneously, previously or subsequently. The MEK inhibitor and a neuraminidase inhibitor preferably are administered contemporaneously. They may be administered as a single formulation or in separate formulations.

The viral disease to be prevented or be treated by the combined administration of a MEK inhibitor and a neuraminidase inhibitor of the invention is preferably an infection caused by negative RNA strand virus. More preferably, the viral disease is caused by an influenza virus, even more preferably the viral disease is caused by influenza A or B virus. Influenza viruses are for example: H1N1, H5N1, H7N7, H7N9. Preferably, the viruses do not show or have developed resistance against an neuraminidase inhibitor. More preferably, the viruses do not show or have developed resistance against an neuraminidase inhibitor selected from oseltamivir carboxylate (oseltamivir), oseltamivir phosphate or zanamivir or peramivir, preferably oseltamivir carboxylate or oseltamivir phosphate.

The MEK inhibitors of the invention to be used in combination with a neuraminidase inhibitor are selected preferably from PLX-4032, AZD6244, AZD8330, AS-703026, GSK-1120212, RDEA-119, RO-5126766, RO-4987655, CI-1040, PD-0325901, GDC-0973, TAK-733, PD98059 and PD184352. More preferably are selected from AZD6244, GDC-0973, RDEA119, GSK1120212, AZD8330, RO51267766, RO4987655, TAK-733, PLX-4032 and AS703026. Even more preferably, they are selected from GSK1120212, AZD6244, PLX-4032 or from PD-0325901, AZD-6244, AZD-8330 and RDEA-119.

The neuraminidase inhibitor is preferably selected from oseltamivir carboxylate (oseltamivir), oseltamivir phosphate or zanamivir or peramivir, preferably oseltamivir carboxylate or oseltamivir phosphate.

In the method of the invention wherein the MEK inhibitor and the neuraminidase inhibitor are used in combination, the patient is a mammal or a bird. Examples of suitable mammals include, but are not limited to, a mouse, a rat, a cow, a goat, a sheep, a pig, a dog, a cat, a horse, a guinea pig, a canine, a hamster, a mink, a seal, a whale, a camel, a chimpanzee, a rhesus monkey and a human. Examples of suitable birds include, but are not limited to, a turkey, a chicken, a goose, a duck, a teal, a mallard, a starling, a Northern pintail, a gull, a swan, a Guinea fowl or water fowl to name a few. Human patient are a particular embodiment of the present invention. A human patient is a particular embodiment of the present invention.

Hence, the present invention provides a method for the prophylaxis and/or treatment of a viral disease comprising administering a MEK inhibitor in combination with oseltamivir or oseltamivir phosphate to a patient in need thereof.

Hence, the present invention provides a method for the prophylaxis and/or treatment of a viral disease comprising administering a MEK inhibitor in combination with zanamivir to a patient in need thereof.

Hence, the present invention provides a method for the prophylaxis and/or treatment of a viral disease comprising administering a MEK inhibitor in combination with peramivir to a patient in need thereof.

A combination according to the invention is CI-1040 or pharmaceutically acceptable salt thereof and oseltamivir preferably oseltamivir phosphate.

A combination according to the invention is PD0325901 or pharmaceutically acceptable salt thereof and oseltamivir preferably oseltamivir phosphate A combination according to the invention is GSK-1120212 and oseltamivir preferably oseltamivir phosphate.

A combination according to the invention is RO5126766 or pharmaceutically acceptable salt thereof and oseltamivir preferably oseltamivir phosphate.

A combination according to the invention is PLX-4032 or pharmaceutically acceptable salt thereof and oseltamivir preferably oseltamivir phosphate.

A combination according to the invention is AZD6244 or pharmaceutically acceptable salt thereof and oseltamivir preferably oseltamivir phosphate.

A combination according to the invention is GDC-0973 or pharmaceutically acceptable salt thereof, and oseltamivir preferably oseltamivir phosphate.

A combination according to the invention is RDEA119 or pharmaceutically acceptable salt thereof and oseltamivir preferably oseltamivir phosphate.

A combination according to the invention is AZD8330 or pharmaceutically acceptable salt thereof and oseltamivir preferably oseltamivir phosphate.

A combination according to the invention is RO4987655 or pharmaceutically acceptable salt thereof and oseltamivir preferably oseltamivir phosphate.

A combination according to the invention is TAK-733 or pharmaceutically acceptable salt thereof and oseltamivir preferably oseltamivir phosphate.

A combination according to the invention is AS703026 or pharmaceutically acceptable salt thereof and oseltamivir preferably oseltamivir phosphate.

A combination according to the invention is PD98059 or pharmaceutically acceptable salt thereof and oseltamivir preferably oseltamivir phosphate.

A combination according to the invention is PD184352 or pharmaceutically acceptable salt thereof and oseltamivir preferably oseltamivir phosphate.

A combination according to the invention is CI-1040 or pharmaceutically acceptable salt thereof and zanamivir or pharmaceutically acceptable salt thereof.

A combination according to the invention is PD0325901 or pharmaceutically acceptable salt thereof and zanamivir or pharmaceutically acceptable salt thereof.

A combination according to the invention is GSK-1120212 or pharmaceutically acceptable salt thereof and zanamivir or pharmaceutically acceptable salt thereof.

A combination according to the invention is RO5126766 or pharmaceutically acceptable salt thereof and zanamivir or pharmaceutically acceptable salt thereof.

A combination according to the invention is PLX-4032 or pharmaceutically acceptable salt thereof and zanamivir or pharmaceutically acceptable salt thereof.

A combination according to the invention is AZD6244 or pharmaceutically acceptable salt thereof and zanamivir or pharmaceutically acceptable salt thereof.

A combination according to the invention is GDC-0973 or pharmaceutically acceptable salt thereof, and zanamivir or pharmaceutically acceptable salt thereof.

A combination according to the invention is RDEA119 or pharmaceutically acceptable salt thereof and zanamivir or pharmaceutically acceptable salt thereof.

A combination according to the invention is AZD8330 and zanamivir or pharmaceutically acceptable salt thereof.

A combination according to the invention is RO4987655 or pharmaceutically acceptable salt thereof zanamivir or pharmaceutically acceptable salt thereof.

A combination according to the invention is TAK-733 and zanamivir or pharmaceutically acceptable salt thereof.

A combination according to the invention is AS703026 or pharmaceutically acceptable salt thereof and zanamivir or pharmaceutically acceptable salt thereof.

A combination according to the invention is PD98059 or pharmaceutically acceptable salt thereof and zanamivir or pharmaceutically acceptable salt thereof.

A combination according to the invention is PD184352 or pharmaceutically acceptable salt thereof and zanamivir or pharmaceutically acceptable salt thereof.

A combination according to the invention is CI-1040 or pharmaceutically acceptable salt thereof and peramivir or pharmaceutically acceptable salt thereof.

A combination according to the invention is PD0325901 or pharmaceutically acceptable salt thereof and peramivir or pharmaceutically acceptable salt thereof.

A combination according to the invention is GSK-1120212 or pharmaceutically acceptable salt thereof and peramivir or pharmaceutically acceptable salt thereof.

A combination according to the invention is RO5126766 or pharmaceutically acceptable salt thereof and peramivir or pharmaceutically acceptable salt thereof.

A combination according to the invention is PLX-4032 or pharmaceutically acceptable salt thereof and peramivir or pharmaceutically acceptable salt thereof.

A combination according to the invention is AZD6244 or pharmaceutically acceptable salt thereof and peramivir or pharmaceutically acceptable salt thereof.

A combination according to the invention is GDC-0973 or pharmaceutically acceptable salt thereof, and peramivir or pharmaceutically acceptable salt thereof.

A combination according to the invention is RDEA119 or pharmaceutically acceptable salt thereof and peramivir or pharmaceutically acceptable salt thereof.

A combination according to the invention is AZD8330 or pharmaceutically acceptable salt thereof and peramivir or pharmaceutically acceptable salt thereof.

A combination according to the invention is RO4987655 or pharmaceutically acceptable salt thereof and peramivir or pharmaceutically acceptable salt thereof.

A combination according to the invention is TAK-733 or pharmaceutically acceptable salt thereof and peramivir or pharmaceutically acceptable salt thereof.

A combination according to the invention is AS703026 or pharmaceutically acceptable salt thereof and peramivir or pharmaceutically acceptable salt thereof.

A combination according to the invention is PD98059 or pharmaceutically acceptable salt thereof and peramivir or pharmaceutically acceptable salt thereof.

A combination according to the invention is PD184352 or pharmaceutically acceptable salt thereof and peramivir or pharmaceutically acceptable salt thereof.

The MEK inhibitor of the present invention may be administered orally, intravenously, intrapleurally, intramuscularly, topically or via inhalation. Preferably, the MEK inhibitor is administered via inhalation or orally.

The neuraminidase inhibitor of the present invention may be administered orally, intravenously, intrapleurally, intramuscularly, topically or via inhalation. Preferably, the neuraminidase inhibitor is administered via inhalation or orally.

When the MEK inhibitor and the neuraminidase inhibitor are in a single formulation, the formulation may be administered orally, intravenously, intrapleurally, intramuscularly, topically or via inhalation. Preferably, the formulation is administered via orally or via inhalation.

Hence, the present invention provides a method of treating viral disease in particular viral disease wherein the infection is caused by a negative RNA strand virus, more in particular a disease wherein the virus is the influenza A or B virus by a combination therapy. In an preferred embodiment of the invention, the virus does not show or have developed resistance to a neuraminidase inhibitor.

The method comprises treating a patient in need of treatment with a therapeutically effective amount of a MEK inhibitor or a pharmaceutically acceptable salt thereof; and simultaneously or sequentially a neuraminidase inhibitor as described below.

In one aspect, a method of treating viral diseases in a patient is provided comprising (1) administering to a patient in need of treatment a therapeutically effective amount of a compound which is a MEK inhibitor or a pharmaceutically acceptable salt thereof; and simultaneously or sequentially (2) administering to said patient a therapeutically effective amount of oseltamivir or oseltamivir phosphate. To put it differently, in accordance with this aspect, the method comprises administering a therapeutically effective amount of a MEK inhibitor or a pharmaceutically acceptable salt thereof to a patient who is under treatment of oseltamivir or oseltamivir phosphate or administering a therapeutically effective amount of oseltamivir or oseltamivir phosphate to a patient who is under treatment with a MEK inhibitor or a pharmaceutically acceptable salt thereof. Preferably the MEK inhibitor is selected from PLX-4032, AZD6244, AZD8330, AS-703026, GSK-1120212, RDEA-119, RO-5126766, RO-4987655, CI-1040, PD-0325901, GDC-0973, TAK-733, PD98059 and PD184352 or a pharmaceutically acceptable salt thereof for use in simultaneous or sequential combination with a neuraminidase inhibitor such as oseltamivir or oseltamivir phosphate for treating and or preventing a viral disease.

In one aspect, a method of treating viral diseases in a patient is provided comprising (1) administering to a patient in need of treatment a therapeutically effective amount of a compound which is a MEK inhibitor or a pharmaceutically acceptable salt thereof; and simultaneously or sequentially (2) administering to said patient a therapeutically effective amount of zanamivir or a pharmaceutically acceptable salt thereof. To put it differently, in accordance with this aspect, the method comprises administering a therapeutically effective amount of a MEK inhibitor or a pharmaceutically acceptable salt thereof to a patient who is under treatment of zanamivir or a pharmaceutically acceptable salt thereof or administering a therapeutically effective amount of zanamivir or a pharmaceutically acceptable salt thereof to a patient who is under treatment with a MEK inhibitor or a pharmaceutically acceptable salt thereof. Preferably the MEK inhibitor is selected from PLX-4032, AZD6244, AZD8330, AS-703026, GSK-1120212, RDEA-119, RO-5126766, RO-4987655, CI-1040, PD-0325901, GDC-0973, TAK-733, PD98059 and PD184352 or a pharmaceutically acceptable salt thereof for use in simultaneous or sequential combination with a neuraminidase inhibitor such as zanamivir or a pharmaceutically acceptable salt thereof for and or preventing a viral disease.

In one aspect, a method of treating viral diseases in a patient is provided comprising (1) administering to a patient in need of treatment a therapeutically effective amount of a compound which is a MEK inhibitor or a pharmaceutically acceptable salt thereof; and simultaneously or sequentially (2) administering to said patient a therapeutically effective amount of peramivir or a pharmaceutically acceptable salt thereof. To put it differently, in accordance with this aspect, the method comprises administering a therapeutically effective amount of a MEK inhibitor or a pharmaceutically acceptable salt thereof to a patient who is under treatment of peramivir or a pharmaceutically acceptable salt thereof or administering a therapeutically effective amount of peramivir or a pharmaceutically acceptable salt thereof to a patient who is under treatment with a MEK inhibitor or a pharmaceutically acceptable salt thereof. Preferably the MEK inhibitor is selected from PLX-4032, AZD6244, AZD8330, AS-703026, GSK-1120212, RDEA-119, RO-5126766, RO-4987655, CI-1040, PD-0325901, GDC-0973, TAK-733, PD98059 and PD184352 or a pharmaceutically acceptable salt thereof for use in simultaneous or sequential combination with a neuraminidase inhibitor such as peramivir or a pharmaceutically acceptable salt thereof for treating and or preventing a viral disease.

In another embodiment, the present invention provides a neuraminidase inhibitor such as oseltamivir, oseltamivir phosphate zanamivir or peramivir or a pharmaceutically acceptable salt thereof for use in combination with a MEK inhibitor such as PLX-4032, AZD6244, AZD8330, AS-703026, GSK-1120212, RDEA-119, RO-5126766, RO-4987655, CI-1040, PD-0325901, GDC-0973, TAK-733, PD98059 and PD184352 or a pharmaceutically acceptable salt thereof for treating and/or preventing a viral disease. Preferably, the MEK inhibitor is GSK1120212 or AZD6244 or PLX-4032.

In the combination therapy methods of the present invention, the MEK inhibitor such as PLX-4032, AZD6244, AZD8330, AS-703026, GSK-1120212, RDEA-119, RO-5126766, RO-4987655, CI-1040, PD-0325901, GDC-0973, TAK-733, PD98059 and PD184352 and the neuraminidase inhibitor such as oseltamivir, oseltamivir phosphate zanamivir or peramivir can be administered at the same time, or separately according to their respective dosing schedules or regimens. When administered at about the same time, the MEK inhibitor and the neuraminidase inhibitor can be administered in the same pharmaceutical composition or in separate dosage unit forms.

For example, in one embodiment of the combination method of the present invention, the compound MEK inhibitor can be administered orally or via inhalation at an effective therapeutic dosage, while the neuraminidase inhibitor can be administered at a dose and dosing schedule as provided in the approved prescribing information or less. Preferably at administered at a lower dosage. For example, according to Tamiflu label, Tamiflu is administered in capsules of 30 mg or 45 mg or 75 mg. A dosage of 75 mg twice daily is the adults and adolescents standard dosage. A lower dosage may be used when Tamiflu is administered in combination with a MEK inhibitor.

In the sequential combination therapies discussed above, preferably the drugs in sequential combination are administered according to their pharmacokinetic profiles such that the second drug is administered after the plasma level of the first drug is substantially reduced or removed.

The pharmacokinetic profiles of the MEK inhibitor and the neuraminidase inhibitor drugs discussed above are generally known in the art.

The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, adverse events, and the like, as will be apparent to a skilled artisan. The amount of administration can be adjusted as the various factors change over time.

The pharmaceutical compounds in the method of present invention can be administered in any suitable unit dosage forms. Suitable oral formulations can be in the form of tablets, capsules, suspension, syrup, chewing gum, wafer, elixir, and the like. Pharmaceutically acceptable carriers such as binders, excipients, lubricants, and sweetening or flavoring agents can be included in the oral pharmaceutical compositions. If desired, conventional agents for modifying tastes, colors, and shapes of the special forms can also be included.

For injectable formulations, the pharmaceutical compositions can be in lyophilized powder in admixture with suitable excipients in a suitable vial or tube. Before use in the clinic, the drugs may be reconstituted by dissolving the lyophilized powder in a suitable solvent system to form a composition suitable for intravenous or intramuscular injection.

In accordance with another aspect of the present invention, a pharmaceutical composition is provided, comprising a therapeutically effective amount of a MEK inhibitor as well as a therapeutically effective amount of a neuraminidase inhibitor chosen from the group of oseltamivir, oseltamivir phosphate, zanamivir and peramivir.

In one embodiment, the composition can be in an orally administrable form (e.g., tablet or capsule or syrup etc.) with a therapeutically effective amount (e.g., from 0.1 mg to 2000 mg, 0.1 mg to 1000 mg, 0.1 to 500 mg, 0.1 to 200 mg, 30 to 300 mg, 0.1 to 75 mg, 0.1 to 30 mg) of MEK inhibitor and a therapeutically effective amount (e.g., from 0.1 mg to 2000 mg, 0.1 mg to 1000 mg, 0.1 to 500 mg, 0.1 to 200 mg, 30 to 300 mg, 0.1 to 75 mg, 0.1 to 30 mg) of neuraminidase inhibitor as described above. For example, according to Tamiflu label, it is administered in capsules of 30 mg or 45 mg or 75 mg. A dosage of 75 mg twice daily is the adults and adolescents standard dosage. A lower dosage may be used when Tamiflu is administered in combination with a MEK inhibitor.

In accordance with another aspect of the present invention, a pharmaceutical kit is provided comprising, in a compartmentalized container, (1) a unit dosage form of a MEK inhibitor such as PLX-4032, AZD6244, AZD8330, AS-703026, GSK-1120212, RDEA-119, RO-5126766, RO-4987655, CI-1040, PD-0325901, GDC-0973, TAK-733, PD98059 and PD184352 and (2) a unit dosage form of a neuraminidase inhibitor such oseltamivir, oseltamivir phosphate zanamivir or peramivir. Optionally, the kit further comprises instructions for using the kit in the combination therapy method in accordance with the present invention.

It has been found by the present inventors that the combinations method of the invention are such that provide a synergy in the prevention and/or treatment of viral diseases, in particular in the prevention and/or treatment of an infection caused by a negative RNA strand virus more in particular viral diseases caused by influenza virus. Even more in particular in the prevention and/or treatment of in influenza A or B virus.

The combinations of the invention may be administered in a synergistic amount.

"Synergy" or "synergistic effect" may be defined as an effect that is more than additive (Chou, 2006, Pharmacolog Reviews, 58: 621-681). Synergistic interactions amongst drug combinations are highly desirable and sought after since they can result in increased efficacy, decreased dosage, reduced side toxicity, and minimized development of resistance when used clinically (Chou, 2006). The two most popular methods for evaluating drug interactions in combination therapies are isobologram and combination index (CI) (Zhao et al., 2004, Clinical Cancer Res 10:7994-8004). Numerous studies in both the cancer therapy field and anti-viral therapy field, where drug combinations to counter the development of drug resistance and to minimize drug doses, use the CI index to evaluate synergy. CI is based on the approach of Chou and Talalay 1984 (Adv. Enzyme Regul. 22:27-55) and relies on the median effect principle and the multiple-drug effect equation. CI can readily be calculated using the program CompuSyn (CompuSyn, Paramus, N.J.). Chou himself (Chou 2006) defines an interaction as slightly synergistic if the CI value is 0.85-0.9, moderately synergistic if the CI value is 0.7-0.85, synergistic if the CI value is 0.3-0.7, strongly synergistic if the CI value is 0.1-0.3, and very strongly synergistic if the CI value is <0.1. In cancer therapy literature, the values of CI that define synergism can vary, for example in Lin et al., 2007, Carcinogenesis 28: 2521-2529, synergism between drugs was defined as CI<1, and in Fischel et al., 2006, Preclinical Report 17: 807-813, synergism was defined as CI<0.8. Similar numbers are used in the anti-viral therapy field. For example, in Wyles et al., 2008, Antimicrob Agents Chemotherapy 52: 1862-1864, synergism was defined as CI<0.9 and in Gantlett et al., 2007, Antiviral Res 75:188-197, synergism was defined as CI<0.9. Based on these references, synergism can be defined as CI values of ≤0.9. All of the above-referenced articles are hereby expressly incorporated by reference in their entirety The MEK inhibitor and the neuraminidase inhibitor of the invention may have a synergistic effect in the treatment of a viral disease greater than the additive effect of each of the MEK inhibitor and the neuraminidase inhibitor administered separately or in combination as predicted by a simple additive effect of the two drugs. In such a case, the synergistically effective amount of the MEK inhibitor is less than the amount needed to treat the viral infection if the MEK inhibitor was administered without the neuraminidase inhibitor. Similarly, the synergistically effective amount of the neuraminidase inhibitor is less than the amount needed to treat the viral infection or if the neuraminidase inhibitor was administered without the MEK inhibitor. The synergistic amount of the MEK inhibitor and of the neuraminidase inhibitor may be defined by the synergism factor (CI value). If defined by the synergism factor (CI value) than CI is less than about 0.9, alternatively less than about 0.85, alternatively less than about 0.8, alternatively less than 0.75, alternatively less than about 0.7, alternatively less than about 0.65, alternatively less than about 0.6, alternatively less than about 0.55, alternatively less than about 0.5, alternatively less than about 0.45, alternatively less than about 0.4, alternatively less than about 0.35, alternatively less than about 0.3, alternatively less than about 0.25, alternatively less than about 0.2, alternatively less than about 0.15, alternatively less than about 0.1.

Preferably a synergistic effect is observed against a virus that does not show or has developed a resistance to a neuraminidase inhibitor.

The combined use of a MEK inhibitor and a neuraminidase inhibitor according to the invention provides a beneficial therapeutic effect also in case of viral disease wherein the virus or virus strain shows or has developed a resistance, in particular a resistance to a neuraminidase inhibitor. In addition, the combined used may act to preserve the efficacy of both drugs over time because the development of resistance would not be observed at all or would be delayed in the time.

DEFINITIONS

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or" as used herein.

As used herein the term viral disease includes disease caused by a virus, for example diseases caused by negative RNA strand virus. For example influenza viruses are negative RNA strand viruses; for example influenza A and B virus. The influenza virus or influenza virus strain according to the invention may show or have developed a resistance to one or more neuraminidase inhibitors (e.g. oseltamivir, oseltamivir phosphate, zanamivir or peramivir) or the influenza virus or influenza virus strain according to the invention does show or does not have developed a resistance to one or more neuraminidase inhibitors (e.g. oseltamivir, oseltamivir phosphate, zanamivir or peramivir).

As used herein, the term "pharmaceutically acceptable salts" refers to the relatively non-toxic, organic or inorganic salts of the active compounds, including inorganic or organic acid addition salts of the compound.

BRIEF DESCRIPTION OF THE DRAWINGS

FIG. 1 shows the inhibition of the proliferation of Influenza A viruses due to AS-703026, AZD-6244, PLX-4032, GSL-1120212 RDEA-119 and RO-5126766.

FIG. 6 shows in vitro studies with the MEK-Inhibitor CI-1040 against H5N1 influenza virus.

FIG. 7 shows in vitro studies with the MEK-Inhibitor PD-0325901 against H5N1 influenza virus.

FIG. 10 shows in vitro studies with the MEK-Inhibitor AZD-8330 against H1N1pdm09 influenza virus.

FIG. 13 shows in vitro studies with PLX-4032 (Vemurafenib) against H7N9 influenza virus.

FIG. 14 shows the synergistic effect of simultaneous MEK- and neuraminidase inhibition against influenza B virus

EXAMPLES

Antiviral Compounds

Figure 2A:
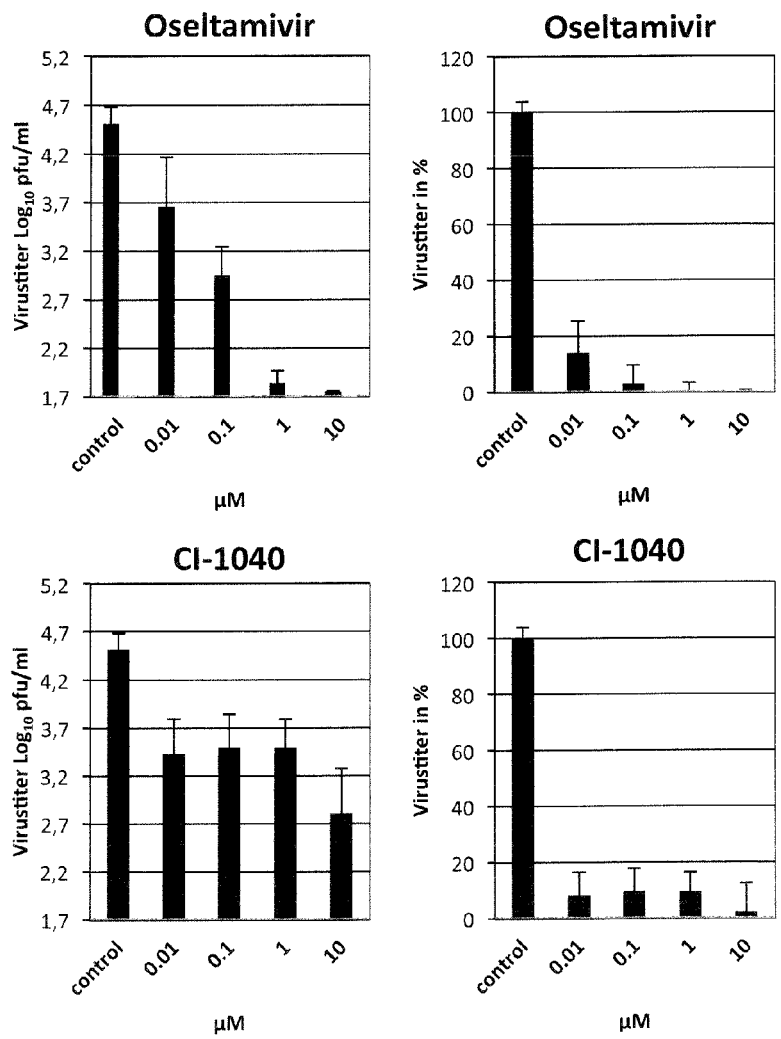
FIGS. 2a-b show the antiviral activity of Oseltamivir, CI-1040 and of Oseltamivir+CI-1040 against influenza virus.

Oseltamivir carboxylate (Oseltamivir) was obtained from Toronto Research Chemicals, Inc. and dissolved in sterile PBS. For in vitro studies the MEK inhibitor CI-1040, PD-0325901, AS-703026, AZD-6244, AZD-8330, PLX-4032, GSL-1120212 RDEA-119 and RO-5126766 were tested. Each MEK inhibitor was dissolved at a stock-concentration of 10 mM in DMSO or suitable solvent. From this solution a dilution series was prepared to attain the desired MEK inhibitor concentration. Because DMSO affects the cell vitality only 1% MEK inhibitor/DMSO solution was given to the medium. Further MEK inhibitors, such as those disclosed herein, can be tested in the same way as the ones referred to herein, either alone or in combination with a neuraminidae inhibitor, such as oseltamivir.

Cell Viability (Cytotoxicity) Analysis

In order to determine whether the concentration of MEK inhibitor used for experiments would affect cell viability, a compound toxicity analysis was performed. MDCK II cells were seeded in 96-well culture plates at a density of $8\times10^4$ cells per well in minimal essential medium (MEM) containing 10% heat-inactivated fetal calf serum (FCS), 100 U/ml penicillin, 100 mg/ml streptomycin. Cells were incubated at 37° C. with 5% CO2 overnight. Thereafter, cells were washed twice with PBS. MEM containing different concentrations of MEK inhibitor (0.001-1000 µM) was added to the cells. After addition of MEK inhibitor, cells were incubated further for 48 h at 37° C. and 5% $CO_2$. Then, cells were fixed by incubation for 30 min at 4° C. with 100 µl 4% paraformaldehyde (PFA). Adding 100 µl crystal violet for 30 min at room temperature stained viable cells. After staining, plates were washed and dried. For the extraction of crystal violet from viable cells 100 µl of 100% methanol was added to each well. After incubation for 30 min at room temperature, the extinction was measured with an enzyme-linked immunosorbent assay (ELISA) reader at OD=490 nm. The percentage of cell viability after treatment with the antiviral compound was calculated as follows: Percent inhibition=100/[OD 490) cell control sample×(OD 490) treated sample]. The $CC_{50}$ value (i.e. the concentration of compound that reduces the cell viability by 50%) was determined with the GraphPad Prism 5 Software by plotting the percent cell viability as a function of compound concentration.

Influenza Virus Titration (AVICEL® Plaque Assay)

Different MEK-inhibitors are available that were already used in clinical trails against cancer (Lorusso et al., 2005; Haura et al., 2010). Therefore, we investigated whether AS-703026, AZD-6244, PLX-4032, GSL-1120212 RDEA-119 and RO-5126766 inhibitors also function as antivirals against influenza virus in MDCKII cell culture.

MDCK II cells and A549 cells were grown with MEM supplemented with 10% calf serum FCS and antibiotics (penicillin and streptomycin). For infection cells were grown overnight in 96-well plates (8×104 cells/well). Immediately before infection the cells were washed with PBS and subsequently incubated with the different influenza A viruses at a MOI of 0.001 for 30 min at 37° C. After the 30 min incubation period the inoculum was aspirated and cells were incubated with either MEM or MEM containing different MEK inhibitor concentrations (1-100 µM). Supernatants were collected at 24 h past infection. To assess the number of infectious particles (plaque/focus titers; pfu) in the collected cell culture supernatants and mice lung homogenates, a Avicel plaque assay was performed in 96-well plate format as described previously (Matrosovich et al., 2006). Virus-infected cells were immunostained by a 1 h incubation with a monoclonal antibody specific for the influenza A virus nucleoprotein (AbD Serotec) followed by 30 min incubation with peroxidase labeled anti-mouse antibody (DIANOVA) and 10 min incubation with True Blue™ peroxidase substrate (KPL). After the reaction was stopped with tap water the plates were dried and scanned with a resolution of 1200 dpi using the CANONFCAN 8800F scanner (Canon). To define the virus titer of the supernatants the plaques/foci of infected cells for every sample in each lane of the 96 well plates were counted. The virus titer is given as the logarithm to the base 10 of the plaques/foci mean value (pfu). The detection limit for this test was <1.7 log 10 pfu/ml. As shown in FIG. 1 the tested MEK inhibitors were able to reduce progeny virus titer after infection of MDCKII cells.

Synergism

To test for synergy between neuraminidase-inhibitor and MEK-inhibitors, the $IC_{50}$ of different MEK-inhibitors in combination with neuraminidase inhibitor against influenza A virus on human lung adenocarcinoma epithelial cells (A549) was evaluated.

Figure 2B:
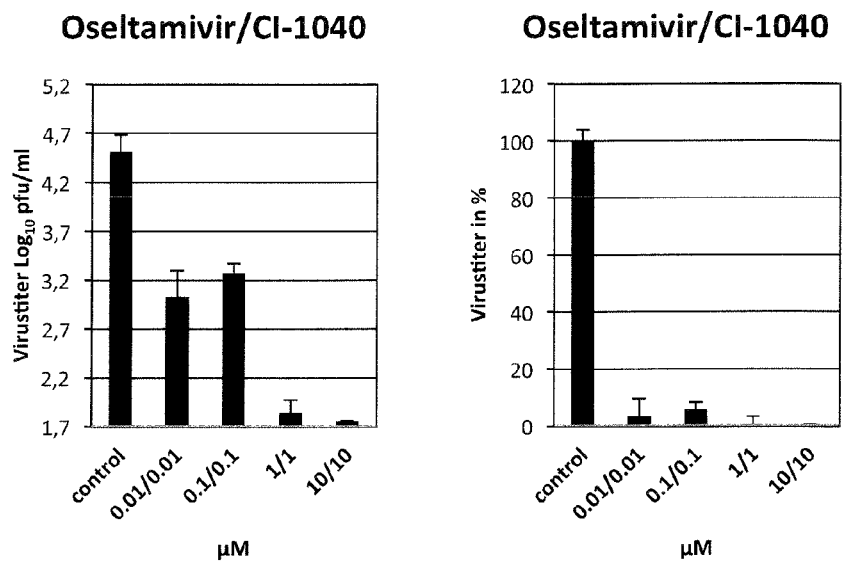
Figure 3A:
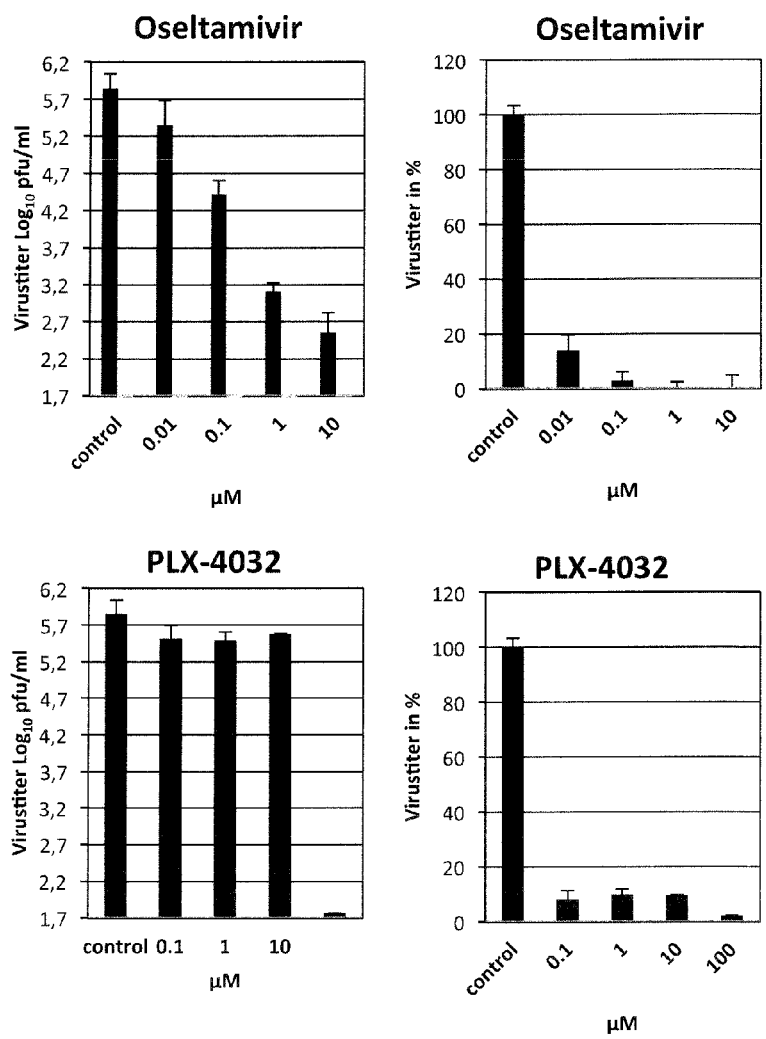
FIGS. 3a-c show the antiviral activity of Oseltamivir, PLX-4032 and of Oseltamivir+PLX4032 at ratio 1:1 and 1:10 against influenza virus.
Figure 3B:
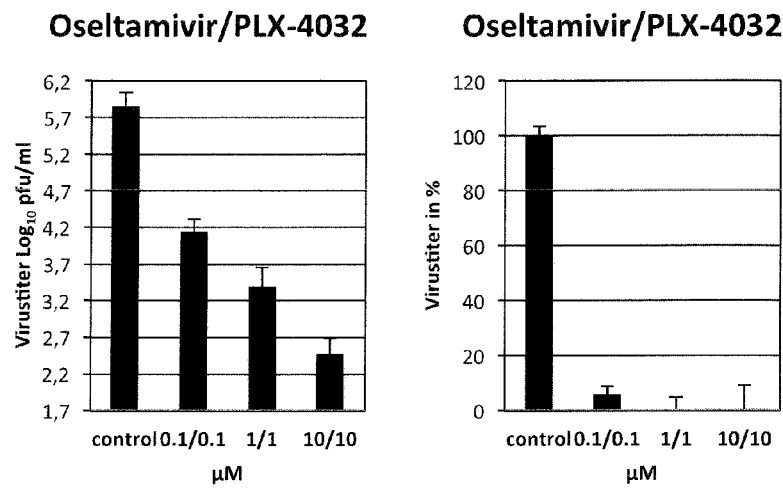
Figure 3C:
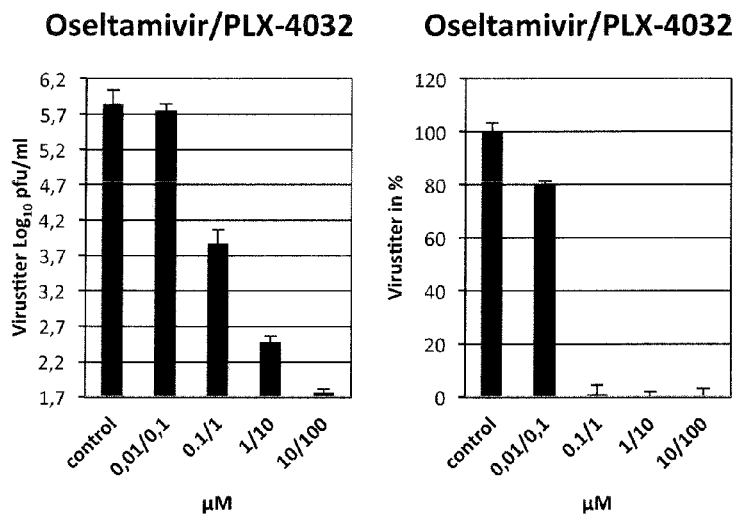

(1) Oseltamivir-carboxylate, CI-1040, and Oseltamivir-carboxylate mixed with CI-1040 in a 1:1 ratio (based on concentration µg/ml) (see FIGS. 2a-b);

(2) Oseltamivir-carboxylate, PLX-4032, and Oseltamivir-carboxylate mixed with PLX-4032 in a 1:1 and 1:10 ratios (based on concentration µg/ml) (see FIGS. 3a, 3b and 3c).

Figure 4A:
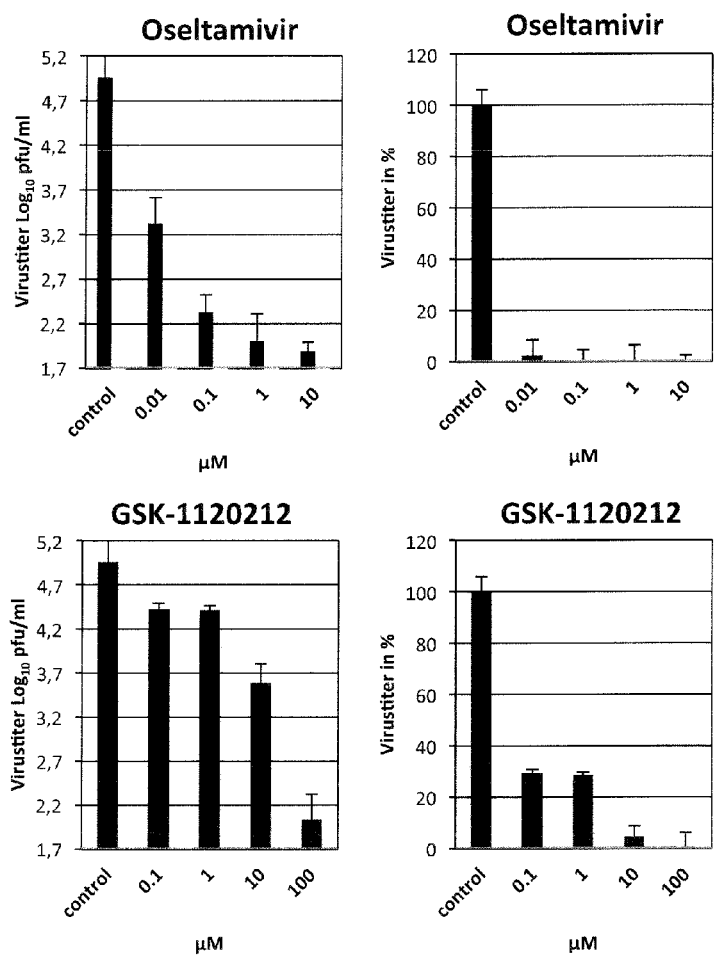
FIGS. 4a-b show the antiviral activity of Oseltamivir, GSK-1120212 and of Oseltamivir+GSK-1120212 at ratio 1:10 against influenza virus.
Figure 4B:
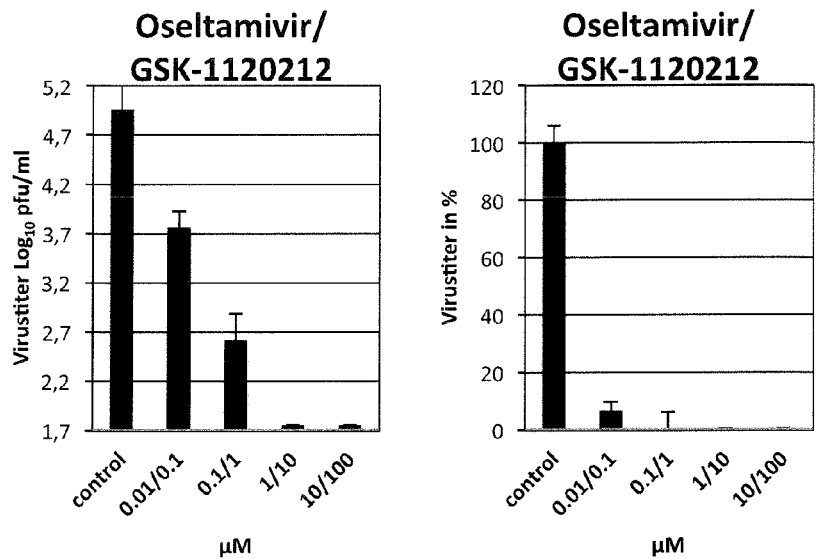

(3) Oseltamivir-carboxylate, GSK-1120212, and Oseltamivir-carboxylate mixed with GSK-1120212 in a 1:10 ratio (based on concentration µg/ml) (see FIGS. 4a and 4b).

Figure 5A:
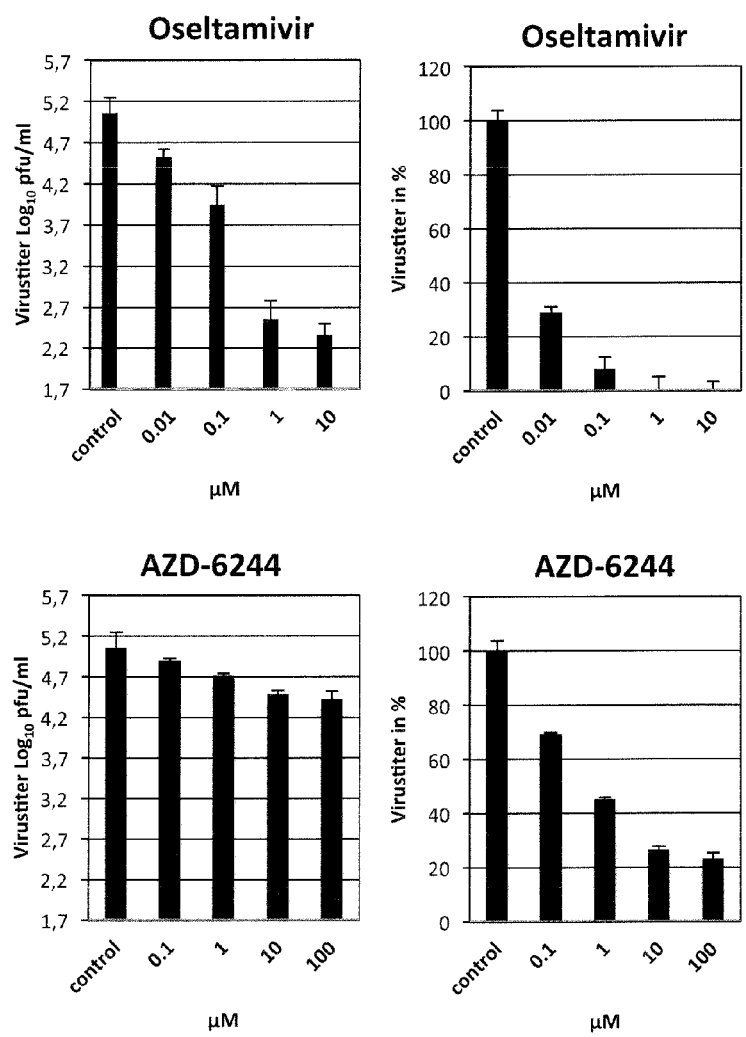
FIGS. 5a-c show the antiviral activity of Oseltamivir, AZD-6244 and of Oseltamivir+AZD-6244 at ratio 1:10 and 1:100 against influenza virus.
Figure 5B:
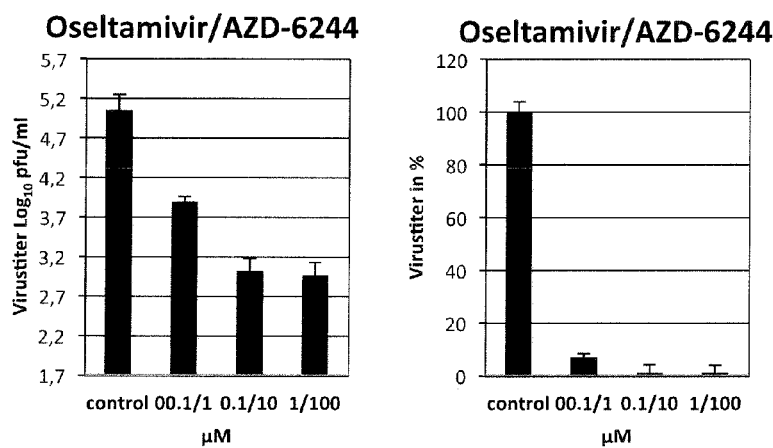
Figure 5C:
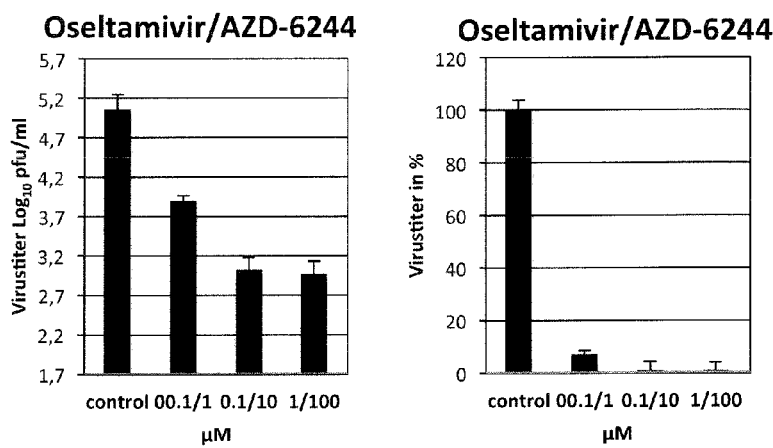

(4) Oseltamivir-carboxylate, AZD-6244, and Oseltamivir-carboxylate mixed with AZD-6244, in a 1:10 and 1:100 ratios (based on concentration µg/ml) (see FIGS. 5a, 5b and 5c).

For each experiment, the CI value at the ED50, ED75, ED90 and ED95 (dose of drug combination that produces an effect, e.g. reduction of virus-titer of 50%, 75%, 90% and 95% in the cell supernatant) was calculated for drug combination. The synergism factors (CI values) for the various combinations are summarized in TABLE 1 below and FIGS. 2b, 3b to 3 c, 4b, 5b and 5c. The CI values have been calculated using the program CompuSyn (CompuSyn, Paramus, N.J.). In all cases for Oseltamivir-carboxylate the CI values were ≤0.53, showing significant synergy between Oseltamivir-carboxylate and all MEK-inhibitors. This synergy unexpected and unique in the field of antivirals against influenza.

TABLE 1

| | Oseltamivir-carboxylate | | | |
|---|---|---|---|---|
| | ED50 | ED75 | ED90 | ED95 |
| CI-1040 | 0.5202 | 0.4010 | 0.3987 | 0.4412 |
| PLX-4032 (1:1) | 0.2783 | 0.3472 | 0.4332 | 0.5036 |
| PLX-4032 (1:10) | 0.2245 | 0.2305 | 0.2367 | 0.2413 |
| AZD-6244 (1:10) | 0.1472 | 0.2086 | 0.2962 | 0.3760 |
| AZD-6244 (1:100) | 0.1140 | 0.1616 | 0.2330 | 0.2993 |
| GSK-1120212 | 0.4874 | 0.4758 | 0.4648 | 0.4576 |

Further In Vitro and In Vivo Studies

In Vitro Studies with the MEK-Inhibitor CI-1040 Against H5N1 Influenza Virus

MDCK II cells were infected with A/Mallard/Bavaria/01/2006 (MB1, H5N1) at a MOI of 0.001. After 30 min. cells were treated with CI-1040 for 24 h.

From FIG. 6 it can be seen that The MEK-Inhibitor CI-1040 is highly potent against different influenza virus strains in cell culture. CI-1040 is also potent against panH1N1 (RB1) and FPV.

In Vitro Studies with the MEK-Inhibitor PD-0325901 Against H5N1 Influenza Virus

MDCK II cells were infected with A/Mallard/Bavaria/01/2006 (MB1, H5N1) at a MOI of 0.001. After 30 min. cells were treated with PD-0325901 for 24 h.

From FIG. 7 it can be seen that The MEK-Inhibitor PD-0325901 is highly potent against H5N1 and different other influenza virus strains in cell culture. PD-0325901 is also potent against panH1N1 (RB1) and FPV.

Oral Treatment of Influenza Virus Infected Mice with CI-1040 or PD-03250901

Eight hours prior infection BL/6 mice were treated (per os) with CI-1040, PD-03250901 (25 mg/kg) or solvent. At the time point of infection (A/Regensburg/D6/09, H1N1pdm09, RB1, 5-fold MLD50) mice were treated again, afterwards all eight hours (4 in total). Twenty-four hours after infection lung virus titer were detected. (n=5)

Figure 8:
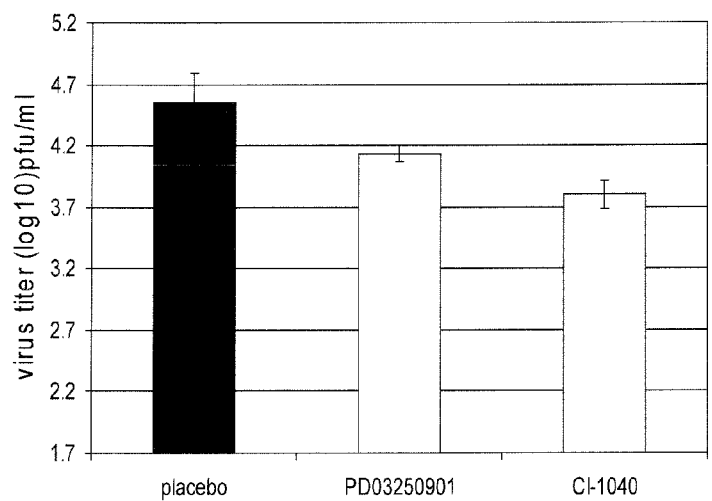
FIG. 8 shows results of the Oral treatment of influenza virus infected mice with CI-1040 or PD-03250901.

From FIG. 8 it can be seen that the MEK-Inhibitors CI-1040 and PD-03250901 are potent in reducing virus titer in the lung of H1N1pdm09 infected mice.

In Vitro Studies with the Dual Raf-MEK-Inhibitor PLX-4032 Against H1N1Pdm09 Influenza Virus A549 cells were infected with H1N1pdm09 (RB1) at a MOI of 0.001. After 30 min. cells were treated with PLX-4032 or OC for 24 h. The IC50 values were calculated with Graph Pad.

Figure 9:
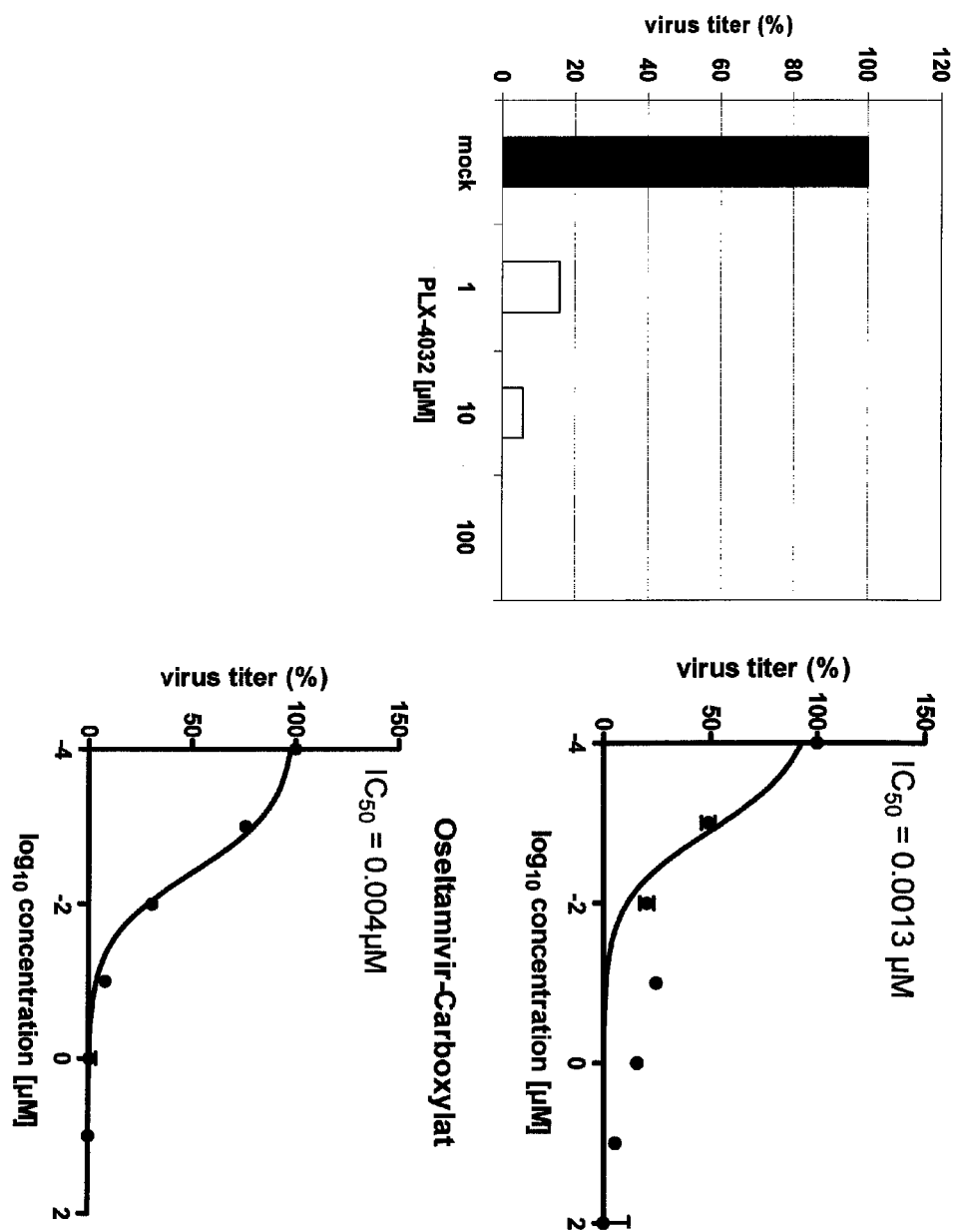
FIG. 9 shows in vitro studies with the dual Raf-MEK-Inhibitor PLX-4032 against H1N1pdm09 influenza virus.
Figure 11:
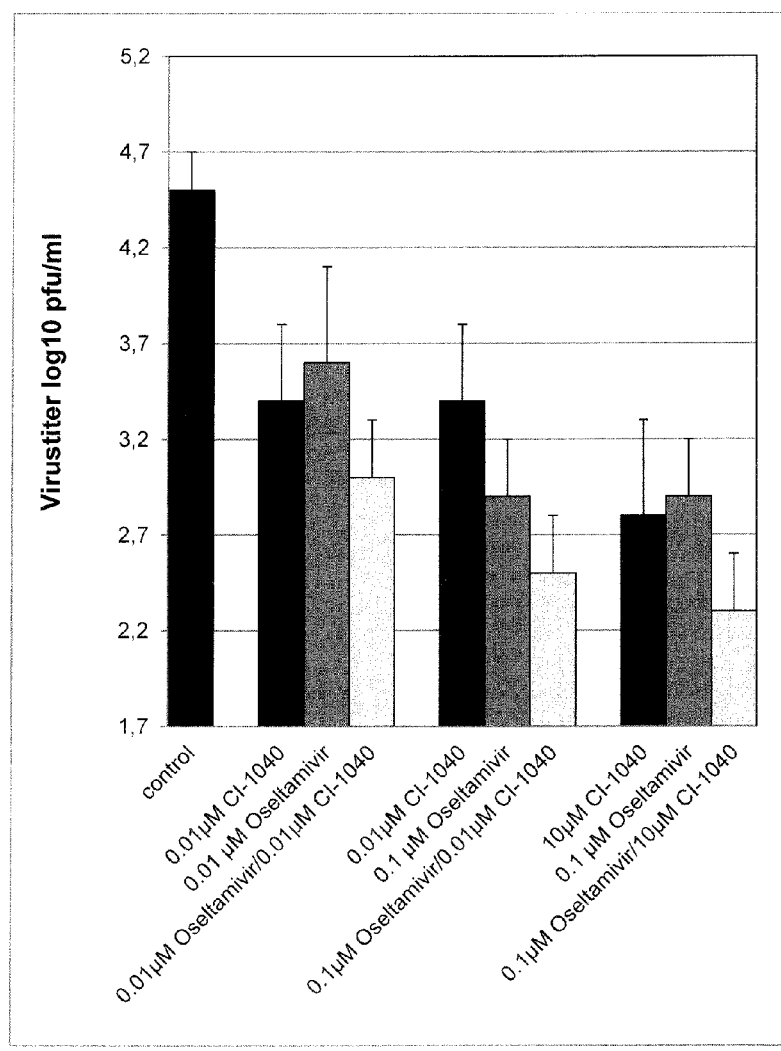
FIG. 11 shows in vitro studies with a combination of CI-1040 and Oseltamivir against H1N1pdm09 influenza virus.
Figure 12:
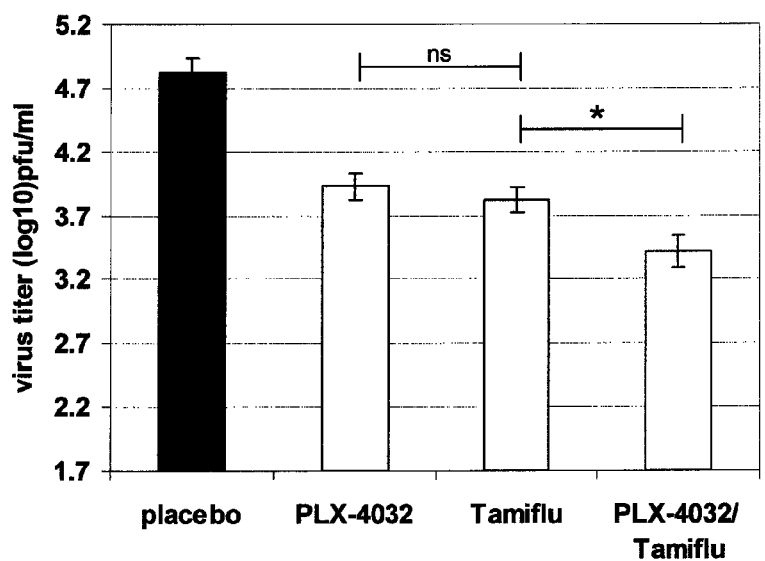
FIG. 12 shows results of the oral treatment of influenza virus infected mice with combination of PLX-4032 and Oseltamivir.

From FIG. 9 it can be seen that the dual Raf-MEK-Inhibitor PLX-4032 is potent against H1N1pdm09 influenza virus.

In Vitro Studies with the MEK-Inhibitor AZD-8330 Against H1N1Pdm09 Influenza Virus A549 cells were infected with H1N1pdm09 (RB1) at a MOI of 0.001. After 30 min. cells were treated with AZD-8330 or OC for 24 h. The IC50 values were calculated with GraphPad.

From FIG. 10 it can be seen that the MEK-Inhibitor AZD-8330 is very potent against H1N1pdm09 in cell culture.

In Vitro Studies with a Combination of CI-1040 and Oseltamivir Against H1N1Pdm09 Influenza Virus A549 cells were infected with H1N1pdm09 (RB1) at a MOI of 0.001. After 30 min. cells were treated with CI-1040 or Oseltamivir alone or in combination for 24 h.

From FIG. 11 it can be seen that a combination of CI-1040 and Oseltamivir against H1N1pdm09 influenza virus is highly potent against H1N1pdm09 in cell culture.

Oral Treatment of Influenza Virus Infected Mice with Combination of PLX-4032 and Oseltamivir Twelve hours prior infection BL/6 mice were treated (per os) with PLX-4032 (50 mg/kg), Tamiflu (5 mg/kg) and solvent alone or in combination (PLX-4032+Tamiflu). At the time point of infection (H1N1pdm09, RB1, 5-fold MLD50) mice were treated again, afterwards all twelve hours (3 in total). Twenty-four hours after infection lung virus titer were detected. (n=5)

It can be seen from FIG. 12 that the combination of PLX-4032 and Oseltamivir (Tamiflu) results in a significant reduction of virus titer in the lung compared to single Oseltamivir (Tamiflu) treatment.

In Vitro Studies with PLX-4032 (Vemurafenib) Against H7N9 Influenza Virus

A549 cells were infected with A/Anhui/1/2013 (H7N9) (moi=0.01) for 30 min and subsequently treated with the indicated amounts of Vemurafenib for 24 h. Data shown in FIG. 13A represent means±SD of at least three independent experiments with two biological samples. Statistical significance was evaluated by Student's t-test (** $p<0.01$).

In FIG. 13B dose-response data depicted in FIG. 13A were used to determine the $EC_{50}$ curve with GraphPad Prism 5 Software. $EC_{50}$=12 μM.

It can be seen from FIGS. 13A and B that PLX-4032 is highly potent against H7N9. Without being bound by theory, PLX-4032 is also highly active against other influenza A virus subtypes.

Synergistic Effect of Simultaneous MEK- and Neuraminidase Inhibition Against Influenza B Virus MDCK-II cells were infected with influenza virus B/Lee/40 at an MOI of 1. After absorption (1 h at RT) media with or without the compounds (MEK inhibitor AZD-8330, neuraminidase inhibitor Oseltamivir) were added at the indicated concentrations (see FIG. 14). The infected cells were incubated for 30 hh at 33° C. At this time point supernatants were collected and the titer of infectious virus particles was determined by focus assay.

It can be seen from FIG. 14 the combination of a MEK inhibitor, such as AZD-8330 and a neuraminidase inhibitor, such as oseltamivir, has a synergistic effect on the inhibition of influenza B virus.

The invention claimed is:

1. A method for treating a subject having a viral infection, comprising: administering to a subject (i) a MEK inhibitor or a pharmaceutically acceptable salt thereof, wherein said MEK inhibitor is selected from the group consisting of AZD6244, AZD8330, GSK-1120212, CI-1040, and PLX-4032, and (ii) a neuraminidase inhibitor or a pharmaceutically acceptable salt thereof, wherein said neuraminidase inhibitor is selected from the group consisting of oseltamivir, oseltamivir phosphate, zanamivir, and peramivir; wherein administering (i) and (ii) treats a viral infection in the subject, and wherein the viral infection is caused by an influenza virus.

2. The method according to claim 1, wherein the influenza virus is influenza A virus or influenza B virus.

3. The method according to claim 1, wherein the MEK inhibitor or a pharmaceutically acceptable salt thereof is administered contemporaneously, previously or subsequently to the neuraminididase inhibitor or pharmaceutically acceptable salt thereof.

4. The method of claim 1 wherein the MEK inhibitor is selected from the group consisting of AZD6244, AZD8330, GSK-1120212, PLX-4032, and CI-1040, or a pharmaceutically acceptable salt thereof, and the neuraminidase inhibitor is oseltamivir or a pharmaceutically acceptable salt thereof.

5. A pharmaceutical composition comprising (i) a MEK inhibitor or a pharmaceutically acceptable salt thereof, wherein said MEK inhibitor is selected from the group consisting of AZD6244, AZD8330, GSK-1120212, CI-1040, and PLX-4032, and (ii) a neuraminidase inhibitor or a pharmaceutically acceptable salt thereof, wherein said neuraminidase inhibitor is selected from the group consisting of oseltamivir, oseltamivir phosphate, zanamivir, and peramivir, for use as a medicament in the treatment of viral infection caused by an influenza virus.

* * * * *